United States Patent
Cohen

(10) Patent No.: US 9,383,369 B2
(45) Date of Patent: Jul. 5, 2016

(54) METHODS FOR IMPROVING FERTILITY AND SELECTIVITY FOR DESIRED OFFSPRING SEX IN ARTIFICIAL INSEMINATION

(75) Inventor: Barb Cohen, Watertown, MA (US)

(73) Assignee: Barb Ariel Cohen, Watertown, MA (US)

( * ) Notice: Subject to any disclaimer, the term of this patent is extended or adjusted under 35 U.S.C. 154(b) by 989 days.

(21) Appl. No.: 12/571,361

(22) Filed: Sep. 30, 2009

(65) Prior Publication Data

US 2011/0076667 A1    Mar. 31, 2011

Related U.S. Application Data

(63) Continuation-in-part of application No. PCT/US2009/039022, filed on Mar. 31, 2009.

(60) Provisional application No. 61/040,717, filed on Mar. 31, 2008, provisional application No. 61/040,798, filed on Mar. 31, 2008.

(51) Int. Cl.
*A01N 1/02* (2006.01)
*G01N 33/68* (2006.01)

(52) U.S. Cl.
CPC ........ *G01N 33/689* (2013.01); *G01N 2800/367* (2013.01)

(58) Field of Classification Search
CPC .................................................. G01N 33/689
See application file for complete search history.

(56) References Cited

U.S. PATENT DOCUMENTS

| | | |
|---|---|---|
| 2005/0114915 A1 | 5/2005 | Cohen et al. |
| 2005/0130115 A1 | 6/2005 | Funk et al. |
| 2005/0192266 A1 | 9/2005 | D'Cruz et al. |

OTHER PUBLICATIONS

Sieme et al., Effects of different artificial inseminatin techniques and sperm doses on fertility of normal mares and mares with abnormal reproductive history, Theriogenology, 2004, vol. 62, p. 915-928.*
Petrella et al., Optimizing incubation conditions for the preservation of sperm motility in processed semen samples, Fertility and Sterility, 2005, vol. 84, p. 513-515.*
Marin-Briggiler et al., Effect of incubating human sperm at room temperature on capacitation-related events., Fertility and Sterility, 2002, vol. 77, p. 252-259.*
Anzar, M. et al. Sperm apoptosis in fresh and cryopreserved bull semen detected by flow cytometry and its relationship with fertility. Biol Reprod. Feb. 2002;66(2):354-60.
International Search Report for PCT/US2010/050881; mailing date Nov. 19, 2010.

* cited by examiner

*Primary Examiner* — Taeyoon Kim
*Assistant Examiner* — Tiffany Gough
(74) *Attorney, Agent, or Firm* — Locke Lord LLP; Bryan D. Zerhusen

(57) ABSTRACT

A method for providing semen optimized for use in artificial insemination is described. Methods involve monitoring sperm cell metabolism by assays that produce results in real time, while sperm are still being processed into doses for use in insemination. Processing is modified in response to assay results, to optimize sperm performance.

24 Claims, 17 Drawing Sheets

Figure 1. Executive Summary of Instant Invention and Background Information

What is the need?
*Dairy farmers need cows, not bulls--but cannot sacrifice fertility*
- Fertility must be maintained because cows must get pregnant to give milk
- A bias in favor of female births—*and* good fertility--offers economic advantage
- The ideal people to meet these needs—if the technology existed to do so--are dairy bull farmers, who collect semen from genetically elite bulls and make many doses from one bull, which they sell to dairy cow farmers for artificial insemination of cows What is the inventive concept?
*It is a way to work with biology by making measurable during sperm processing into doses the changes sperm undergo to prepare to fertilize eggs, as these have a relationship to sperm performance upon insemination of cows*
- Small changes in sex ratio are known to occur naturally in response to environment, so biological mechanisms exist to achieve this
- Let us therefore invent a way to measure relevant biology in real time to produce desirable sperm attributes, so that dairy bull farmers can make use of this added form of process control during preparation of semen into doses for insemination of cows What is the instant invention and results?
*The instant invention is a method of process control for use by dairy bull farmers*
- Preserves fertility
- Creates female bias
- Invisible to farmer—uses stardard AI
- Use on entire herd—heifers (virgin cows) and cows (all previous technologies were for heifers only because they have higher fertility than milking cows who are stressed by lactation What are results?
- 13% increase in females--statistically significant at p = 0.001
- No effect on fertility--statistically indistinguishable from control

Figure 2

Technology Description

*Applicant's Model of Process Control*

Freshly ejaculated sperm cannot fertilize an egg
- A "metabolic marathon" prepares them to function (Yanigamachi et al.)
- Process control prepares them to function optimally in gender bias & fertility (Cohen et al.)

Applicant's Process Control first to create bias and preserve fertility
- Control of naturally-existing ability of biology to create moderate gender bias
- Achieved by taking advantage of maturation differences between X and Y

Assay

- Positive--green fluorescence
- Negative--dark
- Percent positive cells increases with time
- Time of increase differs for each collection
- Time of increase determines processing time
- Assay thus provides process control Figure 4
Current Method of Semen Processing
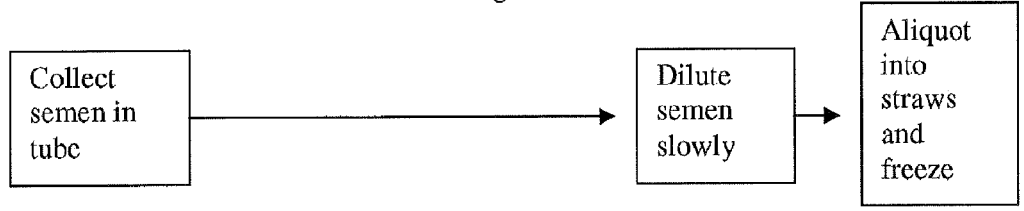
Method of Semen Processing Including Instant Assay
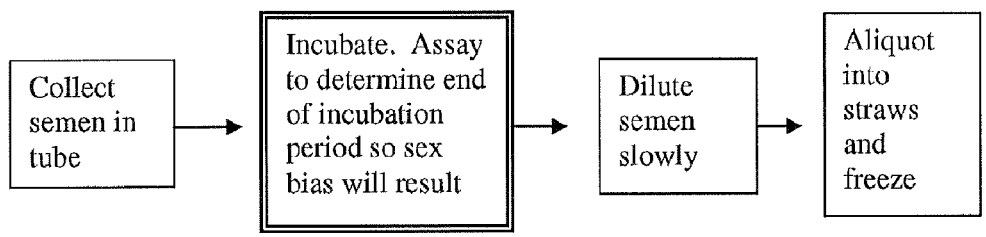

Figure 6

Applicant's Field Data -- Fertility o Both US and EU farmers report fertility uptick
  • Report occurred early in trial (usually indicative of non-subtle difference)
  • Farmers are sensitive to fertility as key parameter of farm health
  • Expectation would be fertility failure for sexing technologies
  • The working model for sexing predicts fertility variation
  • Assay-based fertility improvement produced gain of 2.69% in NRR

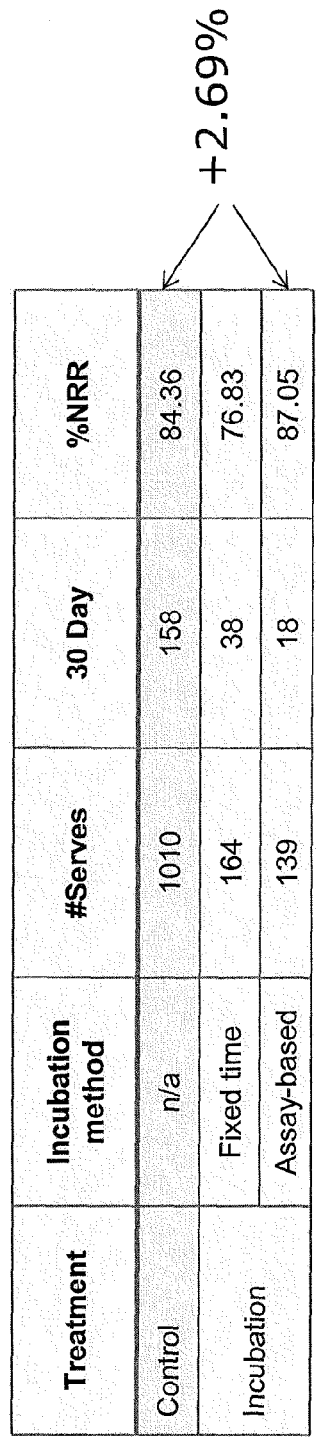

| Treatment | Incubation method | #Serves | 30 Day | %NRR |
|---|---|---|---|---|
| Control | n/a | 1010 | 158 | 84.36 |
| Incubation | Fixed time | 164 | 38 | 76.83 |
| | Assay-based | 139 | 18 | 87.05 |

Applicant's Field Data - - Fertility

- High variability necessitates use of process control assay to measure natural biological processes that increase fertility method
- Time to optimal fertility shows large variation
  - with time of incubation of a single collection
  - between collections from the same bull
- Uptick follows assay, not time of incubation
  - eliminates possibility of settling artifact

| Collection Pair and Bull | Time, h | Method | #Serves | 30 Day | %NRR |
|---|---|---|---|---|---|
| RDU E&F | 5 | Assay | 74 | 8 | 89 |
| | 6 | Fixed | 51 | 11 | 78 |
| QUR I&J | 6 | Fixed | 8 | 2 | 75 |
| | 7 | Assay | 20 | 3 | 85 |
| RDU M&N | 6 | Fixed | 100 | 25 | 75 |
| | 7 | Assay | 39 | 6 | 85 |

*Figure 8*

Applicant's Field Data - - Gender Bias

○ EU farmers report female gender bias uptick
- Report occurred early in trial (usually indicative of non-subtle difference)
- Expectation would be fertility failure for sexing technologies
- The working model for sexing predicts gender variation
- Assay-based gender bias improvement produced gain of 28% in # heifers

| Treatment | Incubation method | # Females | # Males | % Female* |
|---|---|---|---|---|
| Control | n/a | n/a | n/a | 50 |
| Incubation | Fixed time | 34 | 25 | 58 |
| Incubation | Assay-based | 25 | 14 | 64 |

Applicant's Field Data -- Gender Bias

- High variability necessitates use of process control assay to measure natural biological processes that increase fertility
- Time to optimal gender bias shows large variation
  - with time of incubation of a single collection
  - between collections from the same bull
- Uptick follows assay, not time of incubation
  - eliminates possibility of settling artifact

| Collection Cohorts and Bull | Time, h and Cohort | Method | # Females | # Males | % Female |
|---|---|---|---|---|---|
| RDU E&F | 5E | Assay | 15 | 9 | 63 |
|  | 6F | Fixed | 10 | 8 | 56 |
| RDU M&N | 6M | Fixed | 24 | 17 | 59 |
|  | 7N | Assay | 10 | 5 | 67 |

Figure 16
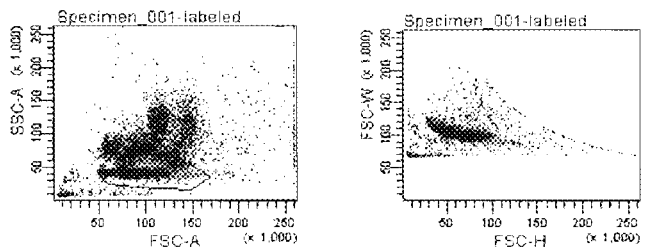
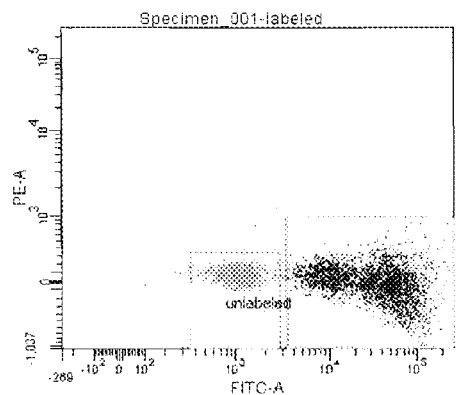
High-throughput by Cytometry
Easy to distinguish sperm as
Negative
Positive
Field-portable cytometers now cost only 30k.

FIGURE 17
Semen processing in the presence and absence of process control by assay:
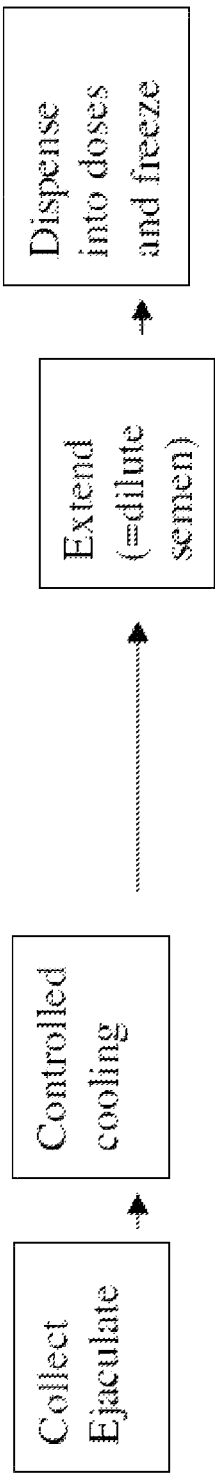
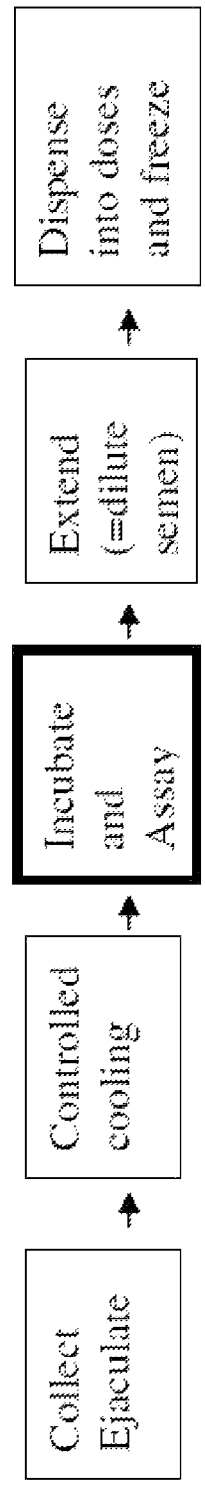
Standard Processing: extension follows cooling with NO process control
Assay-based-Processing: involves incubation time between cooling and extension where metabolism occurs, with incubation time PROCESS-CONTROLLED BY ASSAY

US 9,383,369 B2

METHODS FOR IMPROVING FERTILITY AND SELECTIVITY FOR DESIRED OFFSPRING SEX IN ARTIFICIAL INSEMINATION

This application claims the benefit of PCT/US09/39022, which claims the benefit of U.S. provisional application 61/040,717 filed Mar. 31, 2008 and U.S. provisional application 61/040,798 filed Mar. 31, 2008. The contents of each of these three applications are hereby incorporated by reference in their entirety.

BACKGROUND

Treatment of mammalian semen to achieve a higher proportion of fertility and/or a higher proportion of one gender over another in artificial insemination can be advantageous. For example, a dairy herd would obtain economic and genetic herd quality benefit from an increase in numbers of cows pregnant at any given time and/or birthing a higher percentage of heifers relative to bulls. In such a situation, replacement animals for the herds are produced more efficiently. In addition, especially with low-beef value animals such as Holsteins, the expense of bull calves, and the potential cruelty these animals face when used in veal production is reduced.

The availability of replacement female animals born at the dairy farm eliminates the need to import replacements and the attendant risk of disease introduction into a herd. Additional advantages are found for businesses housing elite sires that produce dairy bull semen. Since these bulls are evaluated, i.e. "sire-proofed," for genetic quality—through their daughters, an elite bull can be brought into semen production more quickly if he produces daughters more quickly and often. This speeds improvement of the sire genotype, with the attendant competitive advantage. This further produces a savings in feed, vet, and other costs associated with bull farming. It also accelerates the improvement of the genetic base of dairy herds using semen from these processors, with the attendant economic savings to dairy farmer and semen processor alike.

In addition, achieving good fertility by increasing the quality of sperm used in artificial insemination is considered to be the single greatest determinant of the success or failure of dairy farms. Since "open" or non-pregnant cows do not lactate and are therefore not productive, they decrease profit. Consequently, any increase in fertility is considered worthwhile. Similar situations exist for other types of animals raised for dairy such as goats, sheep, cattle, buffalo, camels, swine, etc.

In another example, increased sperm quality can lead to improvement and/or expansion of a particular population of animals. For instance, sperm collected from elite race horses or other champion animals, such as cattle or other livestock and particular breeds of dogs and cats, is commonly used for artificial insemination to increase the probability of maintaining particular features in the gene pool. Sperm quality is particularly important in the breeding programs directed to exotic and endangered animals where the number of captive individuals is limited. Here, the ability to increase overall birth rates, thereby increasing the potential for rapid expansion of the population, is critical for success.

In another example, the personal suffering and costs associated with human infertility can in many cases be reduced through increasing sperm quality. Couples whose infertility is caused by low sperm count or poor sperm motility can benefit by increasing the number of intact and viable sperm that result after the washing and preparations steps needed prior to intrauterine artificial insemination (IUI) or intracytoplasmic sperm injection (ICSI).

With respect to gender bias, the suffering and costs of human sex-linked diseases can be reduced through birth of females in affected human families. Female births are the only way to eliminate over 300 X-linked diseases, many of which shorten and impair quality of life and create staggering medical costs. Currently, the costs and suffering associated with these diseases can be decreased through pre-implantation genetic diagnosis. In this process, eggs are harvested by laparoscopy following injections of hormones and fertility drugs. Eggs are fertilized in vitro and, after embryos have reached sufficient size, a single cell is microdissected from each embryo for genetic analysis. A suitable unaffected female embryo is chosen for implantation. Alternatively, sperm is collected and treated with mutagenic dye in preparation for fluorescent activated cell sorting (FACS). X-bearing sperm are obtained, however, they are so damaged that the sperm nucleus must be injected into an isolated egg in vitro using intracytoplasmic egg injection. Embryos are then cultured and implanted in recipients. Both of these techniques are expensive and raise unresolved questions about the effect of exposure to DNA-binding dyes and laser light, with respect to their cytotoxicity and mutagenic potential (Downey et al. (1991) J. Histochem. and Cytochem. 39: 485-489; Durand and Olive (1982) J. Histochem. and Cytochem. 30:111-116).

The scientific literature describes several methods for achieving gender bias through treatment of mammalian semen. They differ in process; some involve physical separation of sperm while others do not. They also differ at point of application; to sperm, to female mammals, to clutches of eggs in egg-laying animals. What they share in common is that they cannot be applied effectively on-site. In addition, with the exception of the instant invention, there is no technology readily used for insemination of cows. Fertility issues with other technologies restrict their use to virgin heifers, which are less stressed and therefore have higher fertility than cows that have experienced the stress of lactation.

For example, several methods are reported for generating sex bias by physical separation of sperm, all of which involve complex laboratory manipulations and equipment. Fluorescence activated cell sorting (FACS) resolves sperm into X (female) and Y (male) bearing pools, after cell labeling with mutagenic DNA-binding dyes to reveal chromosome content (Abeydeera et al. (1998) Theriogenology 50: 981-988; Cran and Johnson (1996) Human Reproduction Update 2: 355-363). Methods of artificially biasing the sex of mammalian offspring through physical separation have also included methods based upon density sedimentation of spermatozoa (e.g. Brandriff et al. (1986) Fertil. Steril. 46:678-685) and by separating the population of spermatozoa into fractions that differ by the sex-linked electrical charge resident thereon (U.S. Pat. No. 4,083,957). Methods have also been described that rely on mechanical sorting of sperm by sex-type. U.S. Pat. No. 5,514,537, for example, uses a column packed with two sizes of beads. The large beads are of a diameter so that the smaller beads will fall between the interstices created between the larger beads. Then the interstices between the smaller beads allow Y-bearing sperm to enter them while the X-bearing sperm are excluded, thereby effecting separation of the two subpopulations. Separation based on immunological methods and cell surface markers have also been proposed (Blecher et al. (1999) Theriogenology 52: 1309-1321). In another example, U.S. Pat. No. 3,687,806 discloses an immunological method for controlling the sex of mammalian offspring using antibodies that react with either X-bearing sperm or Y-bearing sperm which uses an agglutination step to separate bound antibodies from unaffected antibodies. U.S. Pat. No. 4,191,749 discloses a method for increasing the percentage of mammalian offspring of either sex by using a male-specific antibody coupled to a solid-phase immunoabsorbant material to selectively bind male-determining sperm while female-determining sperm remain unbound in a supernatant. U.S. Pat. No. 5,021,244 discloses a method for sorting living cells based upon DNA content, particularly sperm populations to produce subpopulations enriched in X-bearing sperm or Y-bearing sperm by means of sex-associated membrane proteins and antibodies specific for such proteins.

Some methods have combined various aspects of the immunological and mechanical separations such as U.S. Pat. Nos. 6,153,373 and 6,489,092 which use antibodies coupled to a magnetic particle for separation of sperm.

Separation based on a miniscule size difference between X- and Y-bearing sperm has also been attempted (Van Munster et al. (1999) Theriogenology 52: 1281-1293; Van Munster (1999) Cytometry 35: 125-128; Van Munster 2002 Cytometry 47: 192-199).

In addition, sex bias without physical separation of sperm into X and Y bearing classes has been described. For example, stress (Catalano et al. (2006) Human Reproduction 21: 3127-3131), good or poor physical condition (Trivers and Willard (1973) Science 179:90-92), feed composition (Alexenko et al. (2007) Biol. Reprod. 77:599-604), temperature (Crews (1996) Zoological Science 13: 1-13) and other factors (Wedekind (2002) Animal Conservation 5:13-20) have been shown to affect offspring sex ratio.

Lechniak (2003, Reprod. Dom. Anim. 38:224-227); has also shown that time-based production of a sex bias sexing of semen can occur when semen is held for various times before use in insemination for in vitro fertilization. However, the exact time course of activation of sperm from its dormant state at the time of collection, through its various metabolic states of fertility, until the sperm finally become infertile and atophied, varies between different species of mammals, and also between different—individuals of the same species, and even between ejaculates obtained from the same individual animal.

This large degree of variability in time course from semen samples collected from the same individual led those skilled in the art to conclude that a fertile semen sample having a gender bias could not be reliably obtained simply by processing a sample after a standard period of time after collection of the semen sample. Therefore, there is a need in the art to develop a time based assay on which one can reliably depend to provide a semen sample containing sperm which have a desirable trait, such as a fertile, gender biased, semen sample. Ideally, the assay could be performed on site.

SUMMARY

The present invention provides methods of process control for processing semen into doses at AI stations that house elite sires. These methods enable more consistent results for selection of field traits previously desired but unattainable without this process control. The methods include monitoring of the in-process product—collected semen—in real time for processing into finished product (dairy farmers receive semen as doses) at the AI station. The present invention provides a solution to the impediment to desired results because of variability in the metabolic rates of sperm activation, which has hindered the development of a time based assay for obtaining a semen sample having a desired trait, e.g., fertile gender biased sperm. Specifically, the methods described herein involve monitoring, in real time, changes in the metabolic status of sperm in a semen sample. A real time assay of the metabolic status of sperm in an individual semen sample allows a better, more consistent determination of when, after collection of an individual sperm sample, the sperm in the semen sample have the desired traits, e.g., fertility, gender bias. The real time monitoring of the metabolic status of sperm in a semen sample as it progresses through its individual metabolic rate of sperm activation, for example, can be used to determine the real time occurrence of expression of a desired trait in an individual semen sample, such as optimum fertility and/or a gender bias. Advantageously, the methods disclosed herein can be used on site, and are gentle enough that the product can be used to inseminate cows without a loss of fertility that would render the process economically nonviable.

In one embodiment there is a method for obtaining a semen sample with sperm having a desired trait comprising monitoring the metabolic status of said sperm in the sperm sample during incubation, the method comprising the steps of:
i) selecting a marker that can be indicative of a metabolic status of sperm, wherein expression of the marker changes during said incubation;
ii) determining the level of expression of the marker by sperm of the semen sample at a plurality of time points during said incubation, wherein optionally an aliquot of said sample is assayed at each time point;
iii) determining the time point at which the sperm in an aliquot of the semen sample express the marker at about a predetermined level; and
iv) processing said semen sample at a time later than the time point in previous step (iii), wherein said later time is determined by adding a time shift previously established for said marker to the time at the time point determined in previous step (iii),
thereby obtaining sperm with the desired trait.

In another embodiment there is a method for determining a time shift for processing a semen sample by monitoring a change in the metabolic status of sperm in the semen sample during incubation, the method comprising the steps of:
i) selecting a marker that can be indicative of a metabolic status of sperm, wherein expression of the marker changes during said incubation,
ii) determining the level of expression of the marker by sperm of the semen sample at a plurality of time points during said incubation, wherein optionally an aliquot of said sample is assayed at each time point,
iii) determining a time point when the sperm in the semen sample display a maximum level of a desired trait,
iv) selecting a time point (jump point) which occurs before the sperm display the maximum level of the desired trait,
v) determining the level of expression of the marker by sperm in said sample at the selected time point (jump point);
vi) determining the elapsed time between the time point of step (iii) and step (iv),
thereby providing a time shift for a change in the metabolic status between the jump point and the maximum level of the desired trait, as reflected by the marker,
wherein other semen samples can be processed for artificial insemination based on monitoring the marker to the jump point and applying the time shift to determine the desired period for incubation.

In one embodiment there is a method for obtaining a semen sample with sperm having a desired trait comprising moni toring the metabolic status of said sperm in the sperm sample during incubation, the method comprising the steps of:
  i) selecting a marker that can be indicative of a metabolic status of sperm, wherein expression of the marker changes during said incubation;
  ii) determining the level of expression of the marker by sperm of the semen sample at a plurality of time points during said incubation, wherein optionally an aliquot of said sample is assayed at each time point;
  iii) determining the time point at which the sperm in an aliquot of the semen sample express the marker at about a level represented by the jump point of; and
  iv) processing said sample at a later time, wherein said later time is determined by adding the time shift established for the marker, to the time at the time point determined in the immediately previous step (iii);
  thereby obtaining sperm with the desired trait.

In yet another embodiment there is a method for determining the jump point for a particular marker for the metabolic status of sperm in a semen sample during incubation, comprising the steps of:
  i) determining the change in percentage of the sperm displaying a marker/indicator of the metabolic status over time during the incubation or the condition under which the sperm is being held;
  ii) determining when the sperm in the semen sample display significant fertility and/or a significant a significant gender bias and/or a desired trait, where in one embodiment, the sperm in the sample will be capable of producing the desired trait(s) upon artificial insemination in the field;
  iii) selecting a time point (jump point) which occurs before the sperm display a desired trait, and
  iv) determining the percentage of sperm in said sample which display said marker/indicator at the selected time point (jump point);
  thereby monitoring a change in the metabolic status of said sperm in said sample during said incubation, and further determining the jump point for each marker of metabolic status.

In another embodiment, a method for obtaining a semen sample with sperm having a desired trait comprising monitoring the metabolic status of said sperm in the sperm sample during incubation, the method comprising the steps of:
  i) selecting a marker that can be indicative of a metabolic status of sperm, wherein expression of the marker changes during said incubation;
  ii) determining the level of expression of the marker by sperm of the semen sample at a plurality of time points during said incubation, wherein optionally an aliquot of said sample is assayed at each time point;
  iii) determining the time point at which the sperm in an aliquot of the semen sample express the marker at about a maximum level by noticing a drop in expression of said marker; and
  iv) processing said sample at that time;
  thereby obtaining sperm with the desired trait.

Thus, one embodiment described herein is a method for obtaining a semen sample collected, from a male animal, which contains an increased proportion of sperm having a desired trait, by monitoring the metabolic status of said sperm in a sperm sample, comprising the steps of:
  providing a semen sample, which in one aspect has been newly collected from a male, or in another aspect, is a sample which has been frozen or otherwise maintained after collection,
  assaying sperm of said sample over time for expression of a marker indicative of a metabolic stage of said sperm, where in one nonlimiting aspect the assay is performed on an aliquot of the semen sample,
  processing said sample at a predetermined later time point, wherein, at said later time point, the semen sperm of said sample have the desired trait,
  thereby obtaining a sample of sperm with the desired trait.

In one aspect of this embodiment, the desired trait includes, but is preferably not limited to, female gender bias of sperm of the semen sample, male gender bias of sperm of the semen sample, fertility of the semen in the semen sample, and/or a combination of fertility and bias.

In another aspect of this embodiment, the marker includes, but is preferably not limited to, acrosome length or morphology, expression of a cell surface molecule of sperm of the semen sample, electrostatic charge of sperm of the semen sample, and permeability of a dye by sperm or fragments thereof of sperm of the semen sample.

In another aspect of this embodiment, the semen sample is assayed for said marker at intervals ranging from 1, 2, 3, 4, 5, 10, 12, 15, 20, 25, 30, 45, 60, 90 and 120 minutes, which can depend on the rate of change of expression of the marker. In a further aspect, the assay may encompass the use of an aliquot of the semen sample.

In another aspect of this embodiment, the sperm sample is incubated at a constant temperature during said monitoring of the metabolic status.

In another aspect of this embodiment, the marker is selected from, though preferably not limited to, a ligand, a lectin, an enzyme and a receptor, which is expressed on the surface of the sperm, or internally or both. In one embodiment, a ligand includes, but preferably is not limited to, a protein, a glycoprotein, a carbohydrate and a glycolipid. In another embodiment the marker is selected from, though preferably not limited to, acrosome length, acrosome morphology, acrosome ruffling, expression of a cell surface molecule, electrostatic charge of said sperm, and permeability of sperm membrane, a lipid, cholesterol, phosphatidylserine, a sugar and a protein, an intracellular ion, and bicarbonate.

In one embodiment binding of said first ligand evokes the appearance of a secondary marker, which is detected by contacting said secondary marker with a supplemental ligand.

In another nonlimiting aspect of this embodiment, the permeability of a dye by said sperm or fragments thereof is assayed by the intensity of punctate staining by said dye in an aliquot of said sperm sample.

In another aspect of this embodiment, the permeability of said sperm or fragments to a dye is monitored, and the time point selected to process the semen sample is determined with respect to the earlier time point when the sample has the determined intensity of punctate staining by a dye.

In another aspect of this embodiment, the expression of a cell surface marker is monitored, and the time point selected to process the semen sample is determined with respect to the earlier time point when the sample maximally expresses the marker.

In another aspect of this embodiment, the expression of a cell surface marker is monitored, and the time point selected to process the semen sample is determined with respect to the earlier time point when expression of said marker in said sample has decreased relative to its peak expression by a percentage ranging from 95% to 5%.

In another embodiment, the expression of a cell surface marker is monitored, and the time point selected to process the semen sample is measured with respect to the earlier time point when expression of said marker in said sample has increased from its minimal expression by a percentage increase ranging from 5% to 1000% when compared to a prior time point.

In another embodiment, the desired trait is an excess of active female sperm relative to active male sperm in said sample.

In another embodiment, the desired trait is an excess of male sperm relative to female sperm in said sample.

In another embodiment, the desired trait is sperm with optimal fertility.

In one embodiment, the assay is based on the percentage of sperm in the semen sample having a specified marker. In one aspect, the specified marker is a biochemical marker, which is optionally present on the cell surface. Regardless, the marker reflects or is indicative of the metabolic status of the sperm. The marker is not limited to a sperm specific marker.

In one aspect of this embodiment the assay encompasses determining the percentage of sperm in the semen sample having the marker that reflects the metabolic status of the sperm encompasses the steps of a) removing an aliquot from the semen sample; b) contacting the aliquot with a first ligand to said marker; c) detecting binding of said ligand by said sperm; and d) determining the percentage of sperm in said aliquot which binds the ligand. In an alternative aspect of this embodiment, step d) can be replaced by the step of assessing the intensity of punctate binding by a detectable label which binds the marker or the ligand either directly or indirectly.

In one aspect of this embodiment the assay encompasses determining the concentration of said marker detected in sperm of said semen sample comprising: a) removing an aliquot from the semen sample; b) contacting the aliquot with a first ligand to said marker; c) detecting binding of said ligand by said sperm; and d) determining the amount of marker expressed by sperm in said aliquot by quantitating the binding of the marker by the ligand; thereby determining the concentration of said marker detected in sperm of said semen sample.

In another embodiment, the ligand is labeled with visible label.

In another embodiment of this assay, detecting the binding of the ligand by the sperm includes detecting label bound directly or indirectly to the sperm, or fragments of the sperm. In one aspect, a sperm fragment is either associated or disassociated from intact sperm.

In another embodiment, detecting the binding of the ligand by the sperm encompasses contacting the sperm in the aliquot with a second ligand which binds to the first ligand.

In another embodiment, the first ligand and/or the second ligand is an antibody. The antibody can be either polyclonal or monoclonal antibodies, and can comprise one or more labels.

In another embodiment of the methods and assays described herein, an indicator of the metabolic status of the sperm is a biochemical marker. The biochemical indicator includes, but is not limited to, one or more of the following biochemical indicators: a cell surface molecule, an enzyme and a receptor.

In one embodiment, the assay is based on the permeability of sperm or fragments thereof, to dyes, in the semen sample and that reflects, or is indicative of, the metabolic status of the sperm. In one aspect of this embodiment the assay encompasses determining the percentage of sperm in the semen sample having the marker that reflects the metabolic status of the sperm encompasses the steps of a) removing an aliquot from the semen sample; b) contacting the aliquot with a dye; c) detecting accumulation of the dye or staining by the sperm or fragments thereof, and d) determining the percentage of sperm or fragments thereof in said aliquot which accumulate dye (or stain), and/or the intensity of staining and/or the quality of the staining (whether uniform or punctate) of the sperm or fragments thereof in said aliquot by the dye. The intensity can be determined by visual observation.

Definitions

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies, and so forth. Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. See Harlow and Lane, Antibodies: A Laboratory Manual, Cold Springs Harbor Publications, New York, (1988) which are incorporated herein by reference) and chemical methods. Unless otherwise stated, all ranges described herein are inclusive of the specific endpoints. The following terms are provided below.

As used herein, the term "desired trait" with respect to sperm includes, but is preferably not limited to, a physiological characteristic of the sperm. The desired trait can be expressed before fertilization, e.g., the trait of being in a physiologic state capable of fertilization. Alternatively, the desired trait can be expressed after fertilization or both before and after fertilization, e.g., gender of fetus or newborn. The timing of the expression of the desired trait relative to time zero (the time of the collection) varies between semen samples, as illustrated in FIG. 11.

As used herein, the term "semen sample" includes any semen sample collected from an ejaculate of any mammal, including, but preferably not limited to, human, cattle, goats, sheep, buffalo, swine, horses, cats, dogs, rat, mouse, rabbits, hamsters and endangered species of mammals. Preferably the sample is incubated at a constant temperature immediately after collection. Alternatively, the sample is frozen, and later incubated as detailed below.

As used herein, the term "metabolic status" or "metabolic state" or "metabolic stage" is a physiological state of the sperm with respect to specific biochemical and biophysical properties at a specific time point during the incubation period of the sperm sample. Typically, the physiology of sperm changes over time with age, such as the physiological change in fertility of sperm, as illustrated in FIG. 12. Thus, changes in physiology or metabolic state of sperm in a semen sample can include expression of a desired trait, e.g., fertility. Additionally, changes in physiology or metabolic state of sperm in a semen sample can be reflected by expression of one or more markers. In one embodiment of the methods disclosed herein, the expression of one or more markers occurs earlier than the expression of the desired trait. Further, Applicant has discovered that the expression of such markers by sperm in the semen sample occurs at a predetermined time interval, i.e., a predetermined number of minutes or hours, before the expression of the desired trait.

Though the metabolic changes associated with sperm activation is accelerated in Y bearing sperm relative to X bearing sperm, the exact timing of the occurrence of these changes may vary with each individual semen sample. However, the interval between an earlier metabolic state reflected by expression of a marker and the later expression of the desired trait, e.g., fertility, is constant (other conditions, e.g. temperature, being constant). This defined time interval is used in the methods described herein to determine when each individual sample will express the desired trait, e.g., fertility, by monitoring expression of one or more markers. Thus, the time for processing semen into straws can be determined with an increased probability of obtaining the desired trait.

Thus, the phrase "a marker indicative of a metabolic stage of sperm" refers to a measurable attribute of a sperm, including but not limited to a physiological, structural, functional, biochemical and/or electrochemical attribute which reflects the metabolic status of the sperm at a particular time point. The term "marker" includes, but is preferably not limited to, a structural, physical, electrophysical, or biochemical attribute of sperm and/or fragments thereof, including, for example, the nonlimiting examples of acrosome length, sperm morphology (ruffling) of the sperm, expression of a cell surface molecule on the sperm, electrostatic charge of sperm, and permeability by sperm to a molecule, such as, for example, but not limited to, a dye. The term "marker" further includes, but is not limited to, a ligand, a lectin, an enzyme and a receptor, which is expressed on the surface of the sperm, or internally, or both. In some embodiments, the marker is a morphological change in an acrosome which can be viewed, for instance, using bright field microscopy. With respect to acrosome morphology, over time the surface of the acrosome's membrane appears increasingly ruffled. In some embodiments a marker can be cryptic at some stages of metabolism, and not detected.

Preferably, in the present methods, the optimal expression of the desired sperm trait occurs consistently after a constant number of minutes or hours has elapsed from the time that the sperm achieved a specific metabolic state, as illustrated in FIG. 13. Whether the sperm has achieved the specific metabolic state can be assessed by expression of one or more markers by the sperm.

As used herein, the term "antibody," includes, but is not limited to a polypeptide substantially encoded by an immunoglobulin gene or immunoglobulin genes, an IgG antibody, an IgM antibody, or a portion thereof, which specifically bind and recognize an analyte, antigen or antibody. "Antibody" also includes, but is not limited to, a polypeptide substantially encoded by an immunoglobulin gene or immunoglobulin genes, which specifically binds and recognizes the antigen-specific binding region (idiotype) of antibodies produced by a host in response to exposure to the analyte. In one embodiment of the methods described herein, an antibody binds the sperm or fragments thereof, or a primary antibody, through a site on the antibody other than its paratope. In another embodiment, the antibody binds the sperm or fragments thereof, or a primary antibody through its paratope. In another embodiment of the methods described herein, an antibody binds the sperm or fragments thereof, or a primary antibody, both through its paratope and through a site on the antibody other than its paratope.

As used herein, the term "antibody," encompasses polyclonal and monoclonal antibody preparations, as well as preparations including monoclonal antibodies, polyclonal antibodies, hybrid antibodies, altered antibodies, F(ab')$_2$ fragments, F(ab) fragments, F$_v$ fragments, single domain anti bodies, chimeric antibodies, humanized antibodies, dual specific antibodies, bifunctional antibodies, single chain antibodies, and the like, and functional fragments and multimers thereof, which retain specificity for an analyte or antigen. For example, an antibody can include variable regions, or fragments of variable regions, and multimers thereof, which retain specificity for an analyte or antigen. See, e.g., Paul, Fundamental Immunology, 3rd Ed., 1993, Raven Press, New York, for antibody structure and terminology. The antibody or portion thereof, may be derived from any mammalian species, e.g., from a mouse, goat, sheep, rat, human, rabbit, or cow antibody. An antibody or fragments thereof, may be produced synthetically by methods known in the art, including modification of whole antibodies or synthesis using recombinant DNA methodologies, including using phage display libraries.

As used herein, the phrase "binds to" refers to an antibody, reagent or binding moiety's binding of a ligand with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art (for example, by Scatchard analysis). A variety of immunoassay formats can be used to select antibodies specifically immunoreactive with a particular antigen. For example, solid-phase ELISA immunoassays are routinely used to select monoclonal antibodies specifically immunoreactive with an analyte. See Harlow and Lane, Antibodies: A Laboratory Manual, Cold Springs Harbor Publications, New York, (1988) for a description of immunoassay formats and conditions that can be used to determine specific immunoreactivity. Typically a binding reaction will be at least twice background signal to noise and more typically more than 10 to 100 times greater than background.

As used herein, the term "label" includes a detectable indicator, including but not limited to labels which are soluble or particulate, metallic, organic, or inorganic, and may include radiolabels (such as, e.g., $^{14}C$, $^3H$, $^{32}P$), enzymatic labels (e.g., horseradish peroxidase, galactosidase, and other enzyme conjugates), spectral labels such as green fluorescent protein, fluorescent dyes (e.g., fluorescein and its derivatives, e.g., fluorescein isothiocyanate (FITC), Alexa Fluor® 488 Dye, which is a green-fluorescent dyes conjugate with nearly identical spectral properties and quantum yield as fluorescein isothiocyanate, rhodamine, Yo-Pro, a carbocyanine nucleic acid stain sold by Invitrogen, catalog Product V13243, the green-fluorescent YO-PRO®-1), chemiluminescent compounds (e.g., luciferin and luminol), spectral colorimetric labels such as colloidal gold, or carbon particles, or colored glass or plastic (e.g. polystyrene, polypropylene, latex, etc.) beads, as well as dyes, including the cell-permeant pH indicator, carboxy SNARF®-1, an acetoxymethyl ester, acetate which has a pK-a of ~7.5 after de-esterification and is sold by Invitrogen, as catalog # PPLM63-C1270. Where necessary or desirable, particle labels can be colored, e.g., by applying dye to particles.

As used herein, the term "colored particle label" includes, but is not limited to colored latex (polystyrene) particles, metallic (e.g. gold) sols, non-metallic elemental (e.g. Selenium, carbon) sols and dye sols. In one embodiment, a colored particle label is a colored particle that further comprises a member of a conjugate pair. Examples of colored particles that may be used include, but are not limited to, organic polymer latex particles, such as polystyrene latex beads, colloidal gold particles, colloidal sulphur particles, colloidal selenium particles, colloidal barium sulfate particles, colloidal iron sulfate particles, metal iodate particles, silver halide particles, silica particles, colloidal metal (hydrous) oxide particles, colloidal metal sulfide particles, carbon black particles, colloidal lead selenide particles, colloidal cadmium selenide particles, colloidal metal phosphate particles, colloidal metal ferrite particles, any of the above-mentioned colloidal particles coated with organic or inorganic layers, protein or peptide molecules, or liposomes. For example, Quantum dots sold by Invitrogen, is a label encompassed herein.

As used herein, the term "decreased expression" with respect to a marker, refers to a decrease in expression (including a decrease in accessibility or an increase in crypticity) of a marker or given measurable activity (e.g., binding activity, membrane permeability, electrostatic charge) by at least 5% relative to a reference. Such decreased expression is down regulated by at least 5%, 10%, 15%, 20%, 30%, 40%, 50%, 60%, 70%, 80%, 90%, or more, up to and including 100%, i.e., complete absence of the given activity. Decreased expression of a marker can be measured as described in the working examples herein. The term "increased expression" refers to an increase in expression of a marker or given measurable activity (e.g., binding activity, membrane permeability, electrostatic charge) by at least 5% relative to a reference, for example, at least 10%, 15%, 20%, 30%, 40%, 50%, 60%, 70%, 80%, 90%, or even 100%. An increased expression of a marker can be measured as described in the working examples herein.

As used herein, the term "gender bias" with respect to the sperm in a semen sample, refers to a sample having a greater proportion of active, fertile sperm carrying an X chromosome (female gender bias) or a Y chromosome (male gender bias) relative to the proportion of active, fertile sperm carrying an Y chromosome or, an X chromosome, respectively. A gender bias in a semen sample, for example in a semen sample processed in accordance with the methods disclosed herein, may be reflected in the number of relative proportions of male and female offspring generated from an individual semen sample. In preferred embodiments, the gender bias provided by these methods exceeds a gender bias which may be typical of a particular species or individual animal. The methods described herein take advantage of a natural tendency for Y bearing sperm in a semen sample to mature at a faster rate than X bearing sperm, by providing for the identification of when this differential maturation reflects a significant gender bias among sperm with high fertility rates. A particular semen sample will have a gender bias despite the variant rates of sperm maturation found in each collection, but each sample will have the capability of this bias at different times post collection of the ejaculate from the animal.

As used herein, the term "fertility" with respect to sperm in a semen sample, refers to the ability of the sperm to fertilize an egg and create a viable fetus and live-born animal. This ability changes as the sperm age, and changes differentially with respect to whether the sperm is carrying an X chromosome or a Y chromosome.

As used herein, the term "punctate staining" means a distribution of detectable label in the form of distinct spots or points as opposed to a uniform staining across the surface of a sperm or fragments thereof. Quantitative analysis of punctate staining is known in the art, as described for example by Maxim Mokin and Joyce Keifer in "Quantitative analysis of immunofluorescent punctate staining of synaptically localized proteins using confocal microscopy and stereology", Journal of Neuroscience Methods, Volume 157, Issue 2, 30 Oct. 2006, Pages 218-224.

BRIEF DESCRIPTION OF THE FIGURES

FIG. 1. Executive Summary of Instant Invention and Background Information

FIG. 2 Description of Technology

FIG. 4. Comparison of Semen Processing by Standard Methods in the Art and Applicant's Methods.

FIG. 6. Improvement of Fertility using Applicant's methods described herein

FIG. 7 Field Data showing increased fertility using Applicant's methods described herein FIG. 8 Field Data showing increased gender bias using Applicant's methods described herein FIG. 9. Field Data showing increased gender bias using Applicant's methods described herein FIG. 10. Fertility and Gender Bias Increases In Working Dairy Herds (A) bull RDU collection cohorts E (assay-based) and F (fixed time); (B) RDU collection cohorts M (fixed time) and N (assay-based).

DETAILED DESCRIPTION

Figure 3:
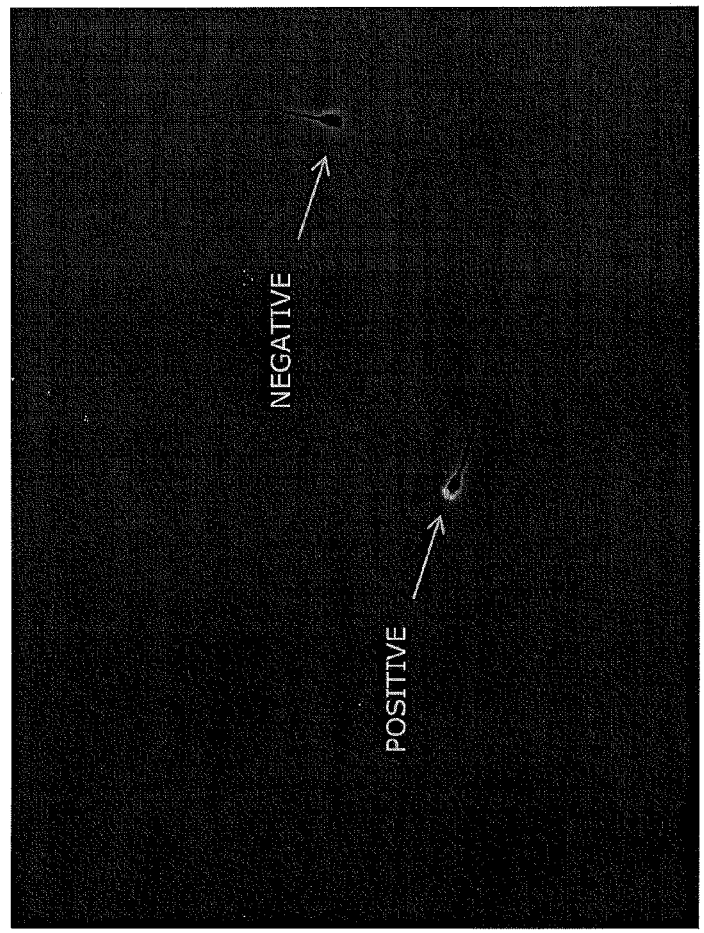
FIG. 3 Fluorescence Assay

Good fertility and replacement female animals are essential to economic health in the dairy industry. The need for female animals remains unmet by gender bias technologies, because they reduce fertility.

A way now exists to address this great market need, as proven by market adoption of the instant invention, with its novel conceptual basis.

Bias in gender ratios of births occurs naturally in response to environmental conditions in mammals. Therefore, biological mechanisms exist to create this bias. The metabolic status of sperm cells at and after insemination is one determinant of gender bias, among others. One could thus theorize that gender bias could be altered in a controlled fashion, if only one could invent a way to evaluate sperm metabolically in real time, while sperm are being collected from dairy bulls and processed by the dairy bull industry into doses to be sold to dairy cow farmers for artificial insemination of cows and heifers (virgin cows).

Such measurement would then become part of the process control steps used to prepare semen doses to service cows. This has analogy in other industries, where one measures specific parameters during manufacturing steps to insure that the product will function well. Currently with sperm, during processing into doses for cows, one measures parameters such as motility and cell number. The instant invention is an assay used to measure attributes of semen in real time during processing that will in the future relate to fertility and/or to gender bias produced by this semen after insemination of cows.

It is well documented in the field that sperm at the time of collection is dormant, and that as it undergoes metabolic changes enabling the sperm to become activated over time. After reaching maximum activation, the sperm continue with their aging process, becoming less fertile, and eventually degrading.

Lechniak et al. (2003, Reprod. Dom. Anim. 38:224-227); incorporated herein by reference in its entirety) describes a study to determine whether or not sperm pre-incubation prior to fertilization in vitro (IVF) influences the sex ratio among blastocysts. The authors reported that when comparisons between groups were made and the actual sex ratios taken into consideration, there were significantly more female-hatched blastocysts among the 24-hour group than among those of either the 0- or 6-hour pre-incubation groups.

The time course of activation of sperm from its dormant state at collection varies not only among individuals within the same species, it also varies between ejaculates obtained from the same individual animal. See FIG. 11. This large degree of variability in the time course of sperm activation led one of skill in the art to conclude that characterizing processes of sperm or obtaining a semen sample with physiology characteristic of a certain time in development such as their fertility or gender bias, was not a process which could be achieved reliably based solely on the time interval after collection of the semen sample.

Thus, described herein are methods that allow one to more accurately determine the time point after collection of the semen sample in which a desired trait is or will be associated with of the sperm relative to an earlier distinct metabolic state. The earlier distinct metabolic state need not have any relevance to the desired trait, other than it occurs at a defined number of minutes or hours before the time point during which the sperm in the semen sample have the desired trait.

Though the metabolic changes associated with sperm activation is accelerated in Y bearing sperm relative to X bearing sperm, the exact timing of the occurrence of these changes varies by up to and including one hour, or by as much as several hours, including up to and including one, two, three, four, five, six, seven, eight, nine, ten, eleven, and twelve hours, or more, with each individual semen sample. However, Applicant has found that the time interval between an earlier metabolic state reflected by expression of a marker and the later expression of the desired trait, e.g., fertility, is constant among individual semen samples collected from various individuals, and/or the same individuals, incubated under the same conditions. This defined time interval is used in the real time methods described herein to determine when each individual sample will express the desired trait, e.g., fertility, by monitoring expression of one or more markers. The time at which the semen sample has the desired traits and can be processed, for example prepared for artificial insemination, for example, can be determined by applying the time interval to the time at which the sperm in the semen sample express a marker at a specific level.

Metabolic state predicts field trait. The concept extends biomarker application to process control, specifically, for a group of cells that move from dormancy to activity then to senescence in ways that affect their field performance and can now be measured. Preferably, the defined metabolic state is easily identified by monitoring for the co-expression of a specified marker(s), or for a specific level of expression of a specified marker(s). Once it is determined the time at which the sperm in the semen sample achieved this metabolic state, (also called a jump point), one can determine the later time point when sperm in the semen sample will have the desired trait, by applying the predetermined defined time interval between expression of the label and the desired trait. Thus, the jump point is the time point from which one calculates when the desired trait will be expressed in the collected semen sample, by adding the time defined in the predetermined time interval. See FIG. 13.

Figure 11:
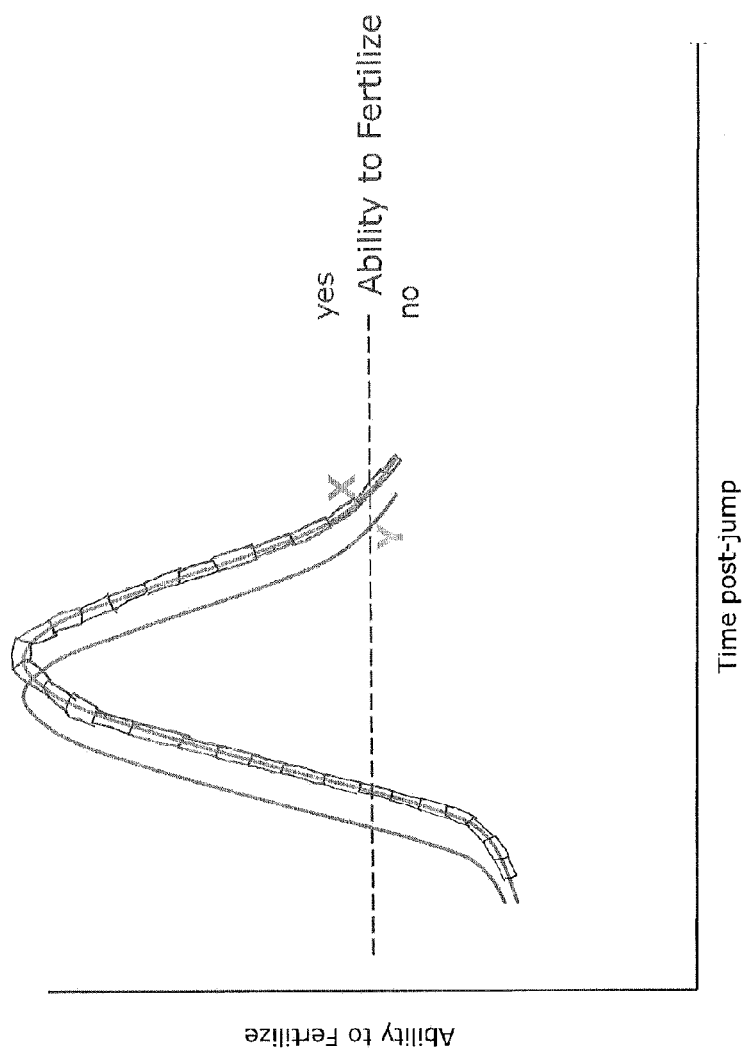
FIG. 11. Y Sperm Gains—and loses—the Ability to Fertilize before X does
Figure 12:
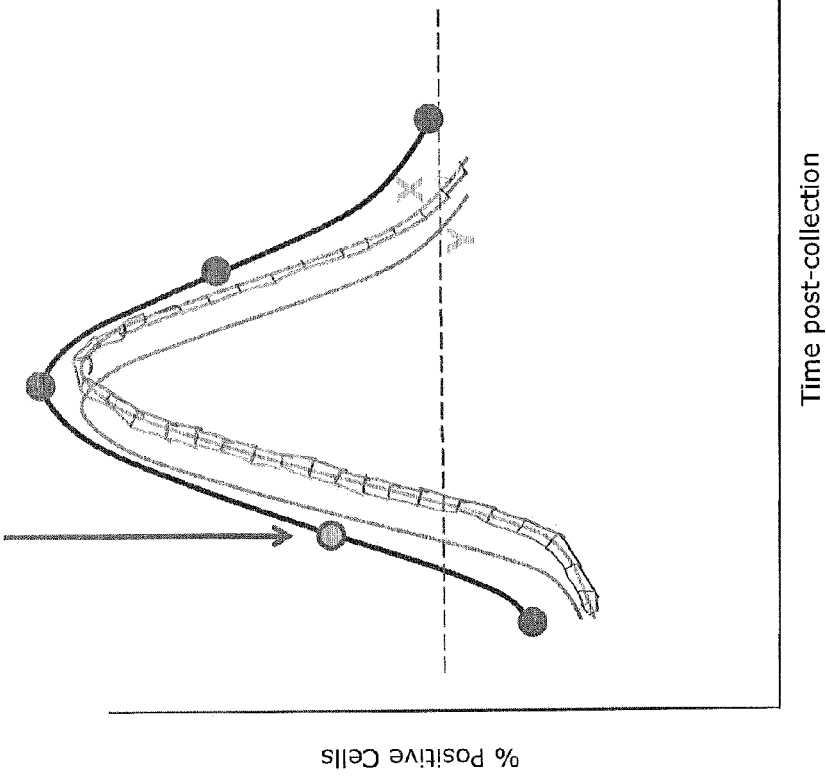
FIG. 12 Assay shows that metabolic status of sperm changes with age.

For example, FIG. 11 reflects the prior art's teaching that sperm carrying a Y chromosome attain—and then lose—their peak ability for fertilization earlier than do sperm carrying an X chromosome. Attainment of a particular metabolic state requires passage of time—an amount of time that differs for every ejaculate. In contrast, Applicant notes that the time between attainment of a specific metabolic state and attainment of specific field traits related to that state is constant across ejaculates. Therefore, according to Applicant's working model, by evaluating the timing of metabolic states by assay, and correlating this timing to sperm behavior, it is possible to predict and obtain desired field traits. This is achieved by using the assay to dictate the timing of sperm processing—that is, when sperm are diluted and aliquoted into doses, for final processing steps that preceed artificial insemination.

Since, in accord with the present invention, the time between of the occurrence of an earlier distinct metabolic state of the sperm in the sample (i.e., the "jump point"), and the peak ability for fertilization by sperm carrying a X chromosome, is constant between samples incubated or held under the same conditions, one can determine when any semen sample similarly incubated has, e.g., an increased female gender bias by measuring the time indicated by the graph after the jump point. Processing the semen sample, e.g., for artificial insemination (AI), at this later time point after the jump point, will result in a sample with an increased female gender bias. Similarly, since the time between the jump point and the peak ability for fertilization sperm carrying an X chromosome is constant between samples, one can determine when any semen sample similarly incubated has an increased female gender bias by measuring the time indicated by the graph between the jump point and the peak fertility of male sperm.

Method of Obtaining a Graph Defining the Relationship Between the Jump Point and the Later Time Point when the Sperm in the Incubated Semen Sample Express the Desired Trait.

Described herein are methods to establish the constant, predetermined defined time interval between expression of a marker and a desired trait. Because, as Applicant has discovered, this interval is constant between individual samples incubated or held under the same conditions, the time interval can be established for use in any sample of the same species/strain of animal, based on the establishment of the time interval in a single semen sample. Thus this interval can be applied to individual semen samples regardless of their individual variations in how quickly the sperm in each semen sample begin sperm activation.

A graph such as that illustrated in FIG. 13, defining the relationship between the jump point and the later time point when the sperm in the incubated semen sample express the desired trait, can be obtained by monitoring a change in the metabolic status of sperm in a semen sample during the incubation period after its collection. The semen sample is collected and incubated, and the metabolic status is monitored during the incubation period, encompassing in one embodiment, the following steps of:

i) determining the change in percentage of the sperm displaying a marker/indicator of the metabolic status over time during the incubation or the condition under which the sperm is being held;

ii) determining when the sperm in the semen sample display significant fertility and/or a significant a significant gender bias and/or a desired trait, iii) selecting a time point (jump point) which occurs before the sperm display a desired trait, and iv) determining the percentage of sperm in said sample which display said marker/indicator at the selected time point (jump point); thereby determining when the jump point occurs for each marker.

This method allows one to determine the constant time interval, between when a desired trait of the sperm in an individual semen sample occurs relative to an earlier discrete metabolic state of the sperm in the semen sample, a metabolic state that can easily be detected by expression of a marker of any measurable type.

Once the relationship between the jump point and the time interval in which the sperm have a desired trait is determined for each species or each donor, the relationship can be used to determine when the semen sample is most likely to contain sperm having a desired trait, so that the semen sample can be further processed. That is, the incubation of the semen sample can be stopped for further processing, or for storage, etc., at the predetermined time after the jump point.

Using a collection method in which the relationship between the jump point of expression of a specified marker indicative of sperm metabolism, and the later time interval in which the sperm have a desired trait has been determined, allows one to more reliably use a time based assay for overcome the high variability of semen metabolic rates across ejaculates (collections) used in artificial insemination (AI) thereby obviating a source of significant problems. Such a method provides for the ability to monitor the biological processes of sperm in a semen sample during real time. This real time monitoring provides a means to tailor semen processing to each individual collection, so that the semen sample is processed when the desired trait is prevalent, and/or optionally differentially expressed, as discussed, for example, in the next section.

Obtaining the Sample with the Desired Trait

Once the constant, defined time interval between the jump point (expression by a particular marker(s) reflecting a distinct homeostatic state) and the later time point when the sperm in the incubated semen sample express the desired trait has been established, as described above, the optimum time point for processing the sperm in an individual semen sample that have a desired trait, such as a gender bias, can be determined by a simple assay. The assay involves monitoring the one or more markers to determine when the jump point occurs in the individual semen sample of interest.

Specifically, the optimum time point for processing the sperm in the particular semen sample that have a desired trait, is based on i) the individual timing of the jump point in the particular sample, and ii) the constant, predetermined time interval between the jump point of expression by a particular marker and the later time point when the sperm in the incubated semen sample express the desired trait.

Thus, in one embodiment, aliquots of the sample can be removed from the semen sample of interest at various time points and assayed for expression of the specific marker(s) so that the timing of the jump point for the semen sample of interest can be established. The optimum time point for processing the sperm in the particular semen sample is then determined by simply waiting the number of minutes/hours specified by the pre-determined time interval between the jump point and the later time point when the sperm in the semen sample of interest express the desired trait.

The monitoring encompasses the following steps using the obtained semen sample of:

i) determining the percentage of sperm in the semen sample having a marker/indicator of its metabolic status during incubation post collection at various time points; and ii) determining the time point (jump point) at which a specified percentage of sperm (or a specified change in the percentage of sperm) in the semen sample have the marker/indicators; where the jump point precedes the interval during which the semen have the desired trait, such as gender bias and/or fertility, by a defined amount of time as described above.

The defined amount of time can be determined by the first method described in this section. Thus, if it is known, for example, that the optimum fertility occurs two hours after the sperm in the sample have attained a specific metabolic status, then one can process the semen sample two hours after the sperm has reached the specific metabolic status (i.e., jump point).

As discussed above, the time at which the sperm attains the specific metabolic status varies from sample to sample, but can be detected by assaying for a marker which reflects the specific metabolic status. Aliquots can be taken from the incubated semen sample at regular intervals beginning at the time at which the semen sample is first collected. In one embodiment aliquots are taken every 10 minutes, every 15 minutes, every 20 minutes, every 30 minutes or every 60 minutes. In another embodiment samples are taken at 5 minute intervals. In yet another embodiment aliquots are taken at hour intervals. The interval will depend on conditions of incubation and experience with a particular donor (e.g., bull). In still another embodiment only a single aliquot is taken and used. In some embodiments the sampling times are adjusted based on the change detected. Here, sampling times in collections that are rapidly changing are shortened while sampling times in collections that are changing slowly are lengthened. Sampling times within a single collection can also be varied. They can be lengthened for those times during incubation of a semen sample where metabolic change is slow, and shortened for those times during incubation of a semen sample where metabolic change is fast.

Advantages

Clearly, the full advantage of increased fertility and/or sex selection for farm economics and genetic improvement of the herd base, or for reduction of human disease, has been unreachable due to the lack of an effective fertility and/or gender bias technique suitable for on-site use (e.g., on-farm and in clinics). What is needed is a method that preserves fertility and/or generates a moderate sex bias when used with standard on-farm and in-doctor's office methods of artificial insemination, and eliminates exposure of sperm to mutagens and damaging conditions. An ability to monitor sperm biological processes as they occur during semen processing provides a way to tailor semen processing to each individual collection of semen, thereby optimizing sperm quality and maximizing fertility and/or creating bias. The present assay provides a solution which makes it possible to increase fertility and/or skew the sex ratio of births in methods that is applicable on-site, while simultaneously eliminating exposure of sperm to deleterious conditions and agents.

The methods described herein are designed to capture these advantages. In addition, because the preferred method simply imposes process control on biological processes common to all mammalian sperm, it is broadly applicable. This is especially relevant for breeding of exotic species, including primates, where fertility maintenance is a key factor and is related to the number and quality of cells used during insemination. It is likewise relevant for on-farm use with cattle, sheep, goats and swine or with champion livestock and animals such as race horses and pedigreed dogs and cats, and exotic or endangered species. The technology also has advantages for human users who suffer from fertility issues or sex-linked diseases.

Markers of Metabolic Status

Optimal sperm quality can be defined on the basis of numerous attributes such as number of viable sperm, sperm motility (both the percentage that are motile and the type of motility exhibited), sperm morphology, acrosomal integrity, etc. It is known, for example, that X-bearing sperm are visibly larger than Y-bearing sperm. It is also known that all sperm go through a series of metabolic changes once ejaculation has occurred and the sperm is mixed with plasma from the seminal vesicles and with other fluids. The sperm "maturation" which includes "capacitation" that follows ejaculation is necessary for sperm to achieve fertilizing ability. A number of membrane changes are associated with these processes (Bearer and Friend (1990) *J Elecon Micros Tech.* 16: 281-297).

Sperm Cell Surface Markers

As described herein, the methods of determining when a desired trait is prevalent, and/or optionally differentially expressed by semen in an individual semen sample of interest is determined in part by an assay in which the expression of specified marker(s) is monitored over time. Thus, the metabolic status of semen is reflected by measurement of a marker. In one embodiment, the marker is component of the cell surface of the sperm, e.g., phosphatidylserine. The percent of individual sperm in the semen collection having a high phosphatidylserine concentration can be used as a cell surface marker of a metabolic status of sperm which occurs at a predetermined amount of time before the semen have the desired trait(s). In other embodiments the cell surface expression of marker is assessed using a lectin, an oligosaccharide conjugated to a fluorphore, antibodies, a positively charged protein conjugated to a fluorophore, merocyanine 540, YOPRO-1, or combinations thereof.

In another aspect, membrane permeability reflects changes to the cell surface. Thus, an indicator of the degree of membrane permeability can be reflected in the degree to which molecules cross the membrane and enter the sperm, e.g. the acrosome or the head, and/or become absorbed to the sperm cell surface. These molecules include, but are preferably not limited to, small molecules, dyes, and enzymes. These molecules, in particular the enzymes, can optionally be used together with either soluble or insoluble chromogenic or flurogenic substrates to create a detectable signal. In another aspect, the cell surface changes can be visualized, either directly or through the use of morphological markers, through the use of brightfield ("light") microscopy, and other forms of microscopy, including, but not limited to, phase contrast microscopy.

When antibodies to sperm cell surface markers are used to detect cell surface changes, they can be directly conjugated to a fluorophore or an enzyme. For example, a primary antibody conjugated to an enzyme in conjunction with the enzymatic substrate to produce a colorimetric reaction can be used in the methods described herein.

In some embodiments, the enzyme itself in conjunction with the enzymatic substrate can be used in the absence of an antibody.

Alternatively, a second antibody reactive to the first antibody can be used to increase the sensitivity of detection. The second antibody also can be directly conjugated with a fluorophore or an enzyme. Thus, the percentage of sperm positive (% positive), for binding of the antibodies the cell surface molecule, is in some instances assessed using a primary antibody in conjunction with a secondary antibody that is conjugated to a fluorophore or other detectable label. Numerous suitable antibodies are described in the literature. For example, a monoclonal antibody to human germ cells has been described by Naz et al. (1984; *Science* 225: 342-344), Saxena and Toshimori report a monoclonal antibody to MC31, a cell surface protein that is modified and redistributed during capacitation (2004; *Biol Reprod* 70:993-1000), Mor et al. describe membrane protein that binds heparin (HBSM) (2007; *Biochem Biophys Res Com* 352: 404-409) and Focarelli et al. report that a CD52 antibody presents a different result compared to an anti-gp20 antibody (1999; *European Society of Human Reproduction and Embryology* 5:46-51). A monoclonal antibody, 4B12, has also been reported that recognizes a surface membrane-associated protein located in the acrosomal portion of the spermatozoa that becomes accessible after capacitation (Mollova et al. (2002) *Folia Biologica* (Praha) 48: 232-236). Other molecules for use as markers during the capacitation process for which antibodies can be made are presented in Cohen-Dayag and Eisenbach (1994; *Am J Physiol Cell Physiol* 267:C1167-C1176).

In addition, antibodies that are not unique to sperm cells can be used to monitor sperm cell surface changes. For example, antibodies directed to the antibiotic cloxacillin and antibodies directed to the Calcium binding protein human calponin can be used, as well as antibodies to *Salmonella* species (Difco *Salmonella* H antiserum A-Z product number 224061). In some instances, if a rabbit anti-*salmonella* antibody is used as a first antibody, a goat anti-rabbit IgG can be used as a second antibody. In cases where an enzyme reaction is used to visualize binding, the second antibody is conjugated to an enzyme and its substrate is added as a solution. Nonlimiting examples of enzyme-substrate pairs are peroxidase/hydrogen peroxide, glycosidase/4-methyl-umbelliferyl-glycoside and horseradish peroxidase/TMB (3,3',5,5'-tetramethylbenzidine).

In one embodiment, the assay involves obtaining a semen sample, incubating the semen sample, taking at least one sample or aliquot from the semen sample, assessing sperm quality by contacting the sperm sample with at least a first molecule or ligand that interacts with a cell surface molecule or component, determining the percentage of sperm positive (% positive) for binding the cell surface molecule, optionally determining the point at which the % positive begins to decline, terminating the incubation of the semen sample after a predetermined time measured from the jump point, and processing the semen sample for immediate use or for storage. Semen may be stored in straws, or otherwise, for artificial insemination. The cell surface molecule being detected may be present on the cell surface, and/or may have been previously cryptic, but now accessible for detection through permeability changes or lipid flip-flop (translocation) across the membrane.

With respect to assessing the ability to produce a sex bias in generated offspring, since the timing of many of the changes that occur during maturation or capacitation may occur at a different rate in X-bearing sperm versus Y-bearing sperm, these sperm cell changes, (including changes on the cell surface and/or internally) can be monitored to assess the ability to produce the highest sex bias in generated offspring. This is done by identifying the time at which the largest group of X-bearing sperm will be at their peak—during the critical time post-artificial insemination with respect to fertilizing performance compared to the Y-bearing sperm. Thus sperm cell surface changes allow one to assess the point at which the highest sex bias can be generated upon insemination of, e.g., cows as well as heifers.

Exemplary Detailed Protocol

An outline of two exemplary detailed protocols for obtaining a semen sample having a gender bias using antibodies to salmonella are described as follows.

The first protocol uses light microscopy and fluorescence microscopy.
1. Treat aliquot of incubating semen sample
   i. Into 1.5 ml tube, pipet the following and mix as directed:
   ii. 100 ul GREEN 1
   iii. 20 ul RED 2
   iv. 5 ul BLUE 3, where one or more of the reagents contains a molecule which binds to, or is incorporated in, sperm or a fragment thereof, such as annexin V. mix
   v. 5 ul neat semen, mix gently
2. Incubate treated aliquot
   a. Place tube in dark for 20-30 minutes
3. Wash
   a. Add 1 ml BUFFER
   b. Microfuge 20 seconds
   c. Carefully remove supernatant with 1 ml pipet
4. Score
   a. Add ~200 ul BUFFER to cell pellet and mix gently to resuspend
   b. FOR MICROSCOPE: Transfer ~5 ul to slide and score # positive sperm (green fluorescence on head) and # total cells. Count at least 100 cells. Calculate % positive. (% Positive=[# positive/# total cells]×100)
   c. FOR CYTOMETER: place aliquot of resuspended cells into cytometer tube and analyze on a calibrated cytometer using the methods described herein.
5. Determining time point for processing semen sample
   a. Plot percentage of positive cells. When percent positive increases sharply (usually doubles from one time point to the next) in the timeframe of 3-6 h post-collection, that is the assay jump point (time zero=time of collection).
   b. Wait 2 h after the jump point, and process semen in the standard protocol, with the following change: Ensure that extender is cooled to 12° C. before it is added.

Figure 13:
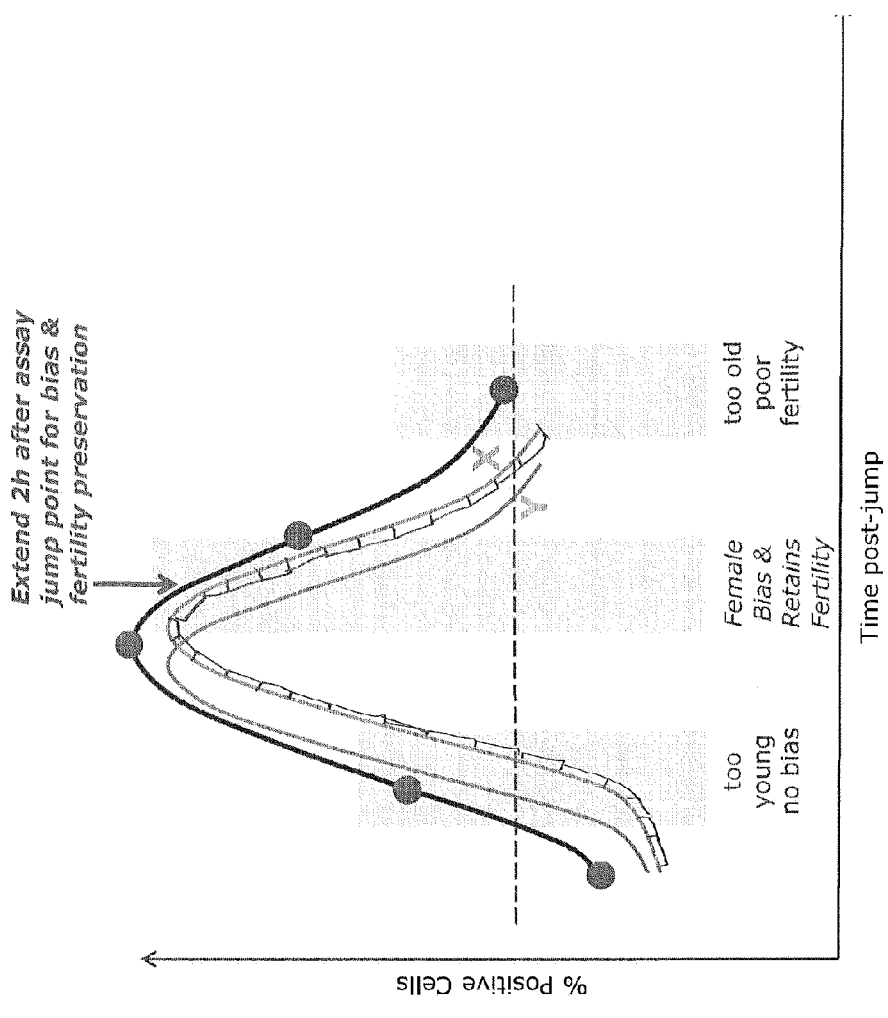
FIG. 13. Process Control uses assay of metabolic status to determine timing of desired trait, e.g. fertility and/or gender bias FIG. 14, Assays show Jump points vary with collection.
Figure 14:
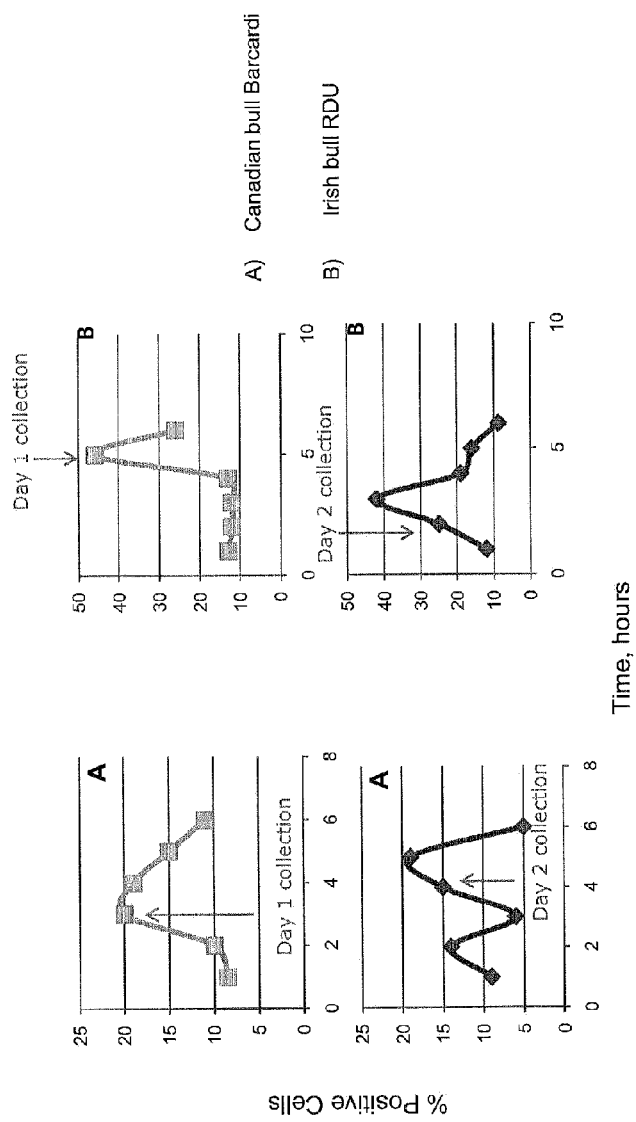
FIG. 14A. uses semen collected from the bull Barcardi.
FIG. 14B. uses semen collected from the bull RDU.
Figure 15:
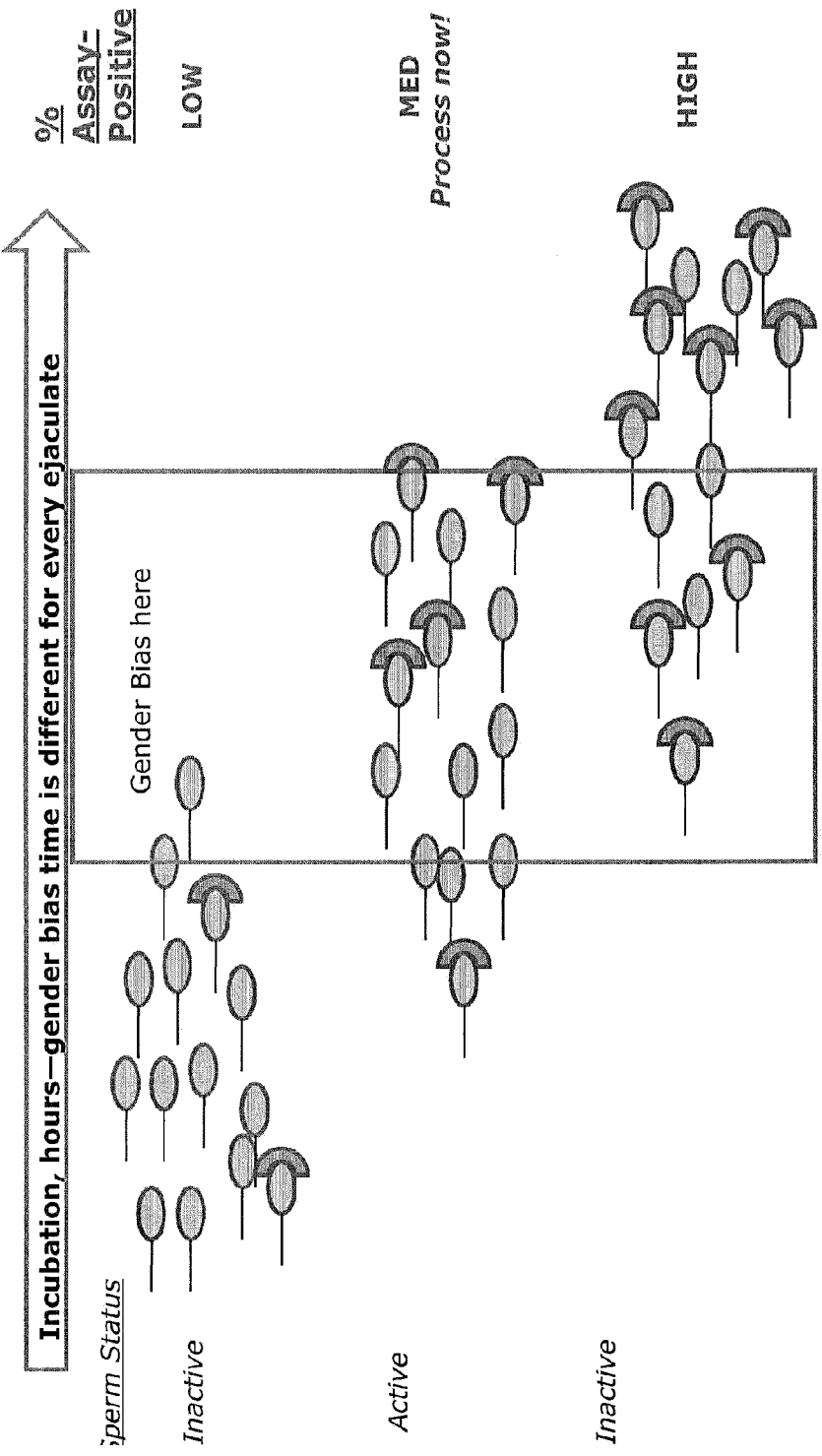
FIG. 15 Applicant's Model of Process Control illustrates that the gender bias is different for every ejaculate FIG. 16 High-through put Cytometry facilitates marker assays described herein FIG. 17. Semen processing in the presence and absence of process control by assay

FIG. 13 provides data obtained with cattle using the above protocol showing that metabolic status changes with age.

The second protocol continues with assessing the staining of the treated aliquot using a cytometer Before running this assay, be sure that semen has been collected and incubated in a manner to minimize process failures.
6. Start Equipment
   i. Turn on computer
   ii. Turn on cytometer
   iii. If needed, empty waste bottle and fill sheath bottle
7. Open Template and Name File
   a. Click appropriate Template
   b. Select File>Save CFlow file as . . .
   c. Name file by date by typing date as yyyymmdd under File Name: (e.g., for Jul. 18, 2009 type: 20090718)
   d. Click Save
8. Collect Data
   a. Under the red Collect tab, click on desired cytometer grid (A1 is for first sample, first bull, A2 is for second sample, first bull. B1 is for first sample, second bull, etc.)
   b. Next to cytometer grid (e.g., A01) type sample information (e.g., RDU-0 for first time point from bull RDU)
   c. Check that stoplight shows green color. Load sample onto SIP tube on cytometer and pull out plastic tube support underneath tube
   d. Click Run
   e. After data are acquired, adjust vertical gate on histogram plot (Plot 3) so that the percentage of positive sperm (the peak on the right) can be determined. Record this number. Remove sample from SIP tube
   f. For the next sample, repeat process above starting with step a
   g. After the samples for that hour are finished, click Backflush, wait for stoplight to show green, then click Unclog
9. Clean and Shut Down Equipment
   a. As desired throughout day, place towel under SIP tube and select Backflush or Unclog
   b. At the end of the day, place a tube of water on the cytometer, select well H11 and click Run. Allow water to clean system for at least 2 minutes. From the pull-down menu, select Instrument>Run cleaning fluid cycle
   c. Turn off cytometer, then turn off computer Visualization of the sperm cell changes, whether at the surface or inside the cell, can be accomplished in numerous different ways. As discussed above, visualization based on the use of a fluorophore or other light emitting molecule, used alone or in combination with a binding protein or antibody. Suitable fluorophores include, but are preferably not limited to, carboxifluorescein acetate, phycoerythrin, calcein acetate, alexa fluor 488, YO-PRO-1, SNARF-1, and combinations thereof. In some embodiments combinations of the fluorophores are used where the range of excitation is similar (e.g. 488 nm), but emission occurs in different areas of the spectrum (e.g. the green wavelength (515 nm) vs. the red wavelength (610 nm)). The use of multiple florophores is particularly useful when more then one marker is being monitored.

The metabolic status of cells can be determined as a function of the cell's permeability to any molecule, such as a dye or stain or other molecules such as enzymes having insoluble chromogenic substrates. Suitable dyes for use in an assay to determine permeability of the cell membrane, or the ability of the cell to pump out or concentrate molecules including but are preferably not limited to, dyes, Annexin-V, Annexin-V-Biotin, biotin, Annexin V-PE, Annexin V-FITC, SAv-FITC, 7-AAD, Hydroethidine, Evans blue, chlorazol Black E, Coomassie Blue and Trypan blue, to name but a few. Combinations of these dyes can also be used. Chromogenic substrates include TMB (3.3',5,5'-tetramethylbenzidine) for peroxidase, ABTS (2.2-Azino-di(3-EthylBenzthiazoline Sulfonic acid) for peroxidase, pNPP (p-nitrophenyl phosphate, disodium salt) for alkaline phosphatase, and 5-bromo-4-chloro-3-indoyl-beta-D-glucuronide (BCIG) for beta galactosidase. Also useful are carboxyfluorescein and phycoerythrin, calcium acetate, Yo-PRO-1, SNARF-1, AlexaFluor-488 and Fluorescein isothiocyanate (FITC).

Below are two detailed protocols for analyzing metabolic changes reflected by changes in membrane permeability of the sperm and/or fragments thereof. The readout is in terms of the quantity of small bright particles similar in size to the particles comprising the punctate staining pattern—the fluorescent crescent—over the acrosomal region of intact sperm.

Treat
  Into 1.5 ml tube, pipet the following and mix as directed:
  100 ul GREEN 1
  20 ul RED 2
  5 ul BLUE 3, mix
  5 ul neat semen, mix gently
Incubate
  Place tube in dark for 20-30 minutes
Wash
  Add 1 ml BUFFER
  Microfuge 20 seconds
  Carefully remove supernatant with 1 ml pipet
Score
  Add ~200 ul BUFFER to cell pellet and close tube
  Mix tube vigorously. This can be done by holding tube top firmly in one hand and striking tube at tube bottom with finger of other hand. Strike tube at least 5 times. Alternatively, a vortex mixer can be used.
  Transfer ~5 ul to slide and evaluate at least 3 fields for appearance of small fluorescent particulates (as evidenced for example by staining) and for torn or partially missing fluorescent crescents on the heads of positive sperm.
  Score assay: no punctate staining=1, slight=2, pronounced=3.
10. Determine time point for processing semen sample
  Upon appearance of a small particle diffuse objects staining at a score of 2 or higher, immediately carry out first step of processing or extension by adding extender to the semen sample
Modification of above protocol
Treat
  Into 1.5 ml tube, pipet the following and mix as directed:
  100 ul GREEN 1
  20 ul RED 2
  5 ul BLUE 3, mix
  5 ul neat semen, mix gently
Incubate
  Place tube in dark for 20-30 minutes
Wash
  Add 1 ml BUFFER
  Microfuge 20 seconds
  Carefully remove supernatant with 1 ml pipet
Score
  Add ~200 ul BUFFER to cell pellet and close tube
  Mix tube vigorously. This can be done by holding tube top firmly in one hand and striking tube at tube bottom with finger of other hand. Strike tube at least 5 times. Alternatively, a vortex mixer can be used.
  Transfer ~5 ul to slide and evaluate at least 3 fields for appearance of small fluorescent particulates (punctate staining) and for torn or partially missing fluorescent green crescents on the heads of positive sperm.
  Score assay: no punctate staining=1, slight=2, pronounced=3.
Determine Processing Time
  Determine the hour when the staining score increases above 1, by using a quantitative scoring system, such as described by Maxim Mokin and Joyce Keifer, supra. Three hours after that time point, end the incubation by carrying out the first extension. (For example, if the staining score is 1 at hour 2 and increases to 2 at hour 3, process semen sample by for example, adding extender at hour 6—where hour zero is the time of collection.) Use extender that is at 12° C. and keep collection cool while processing.

The above protocols, and modifications thereof, have been used extensively by the present inventor with cattle. However, the assay can be used for other species, such as human, in a similar manner. In addition to work with cattle, analysis of human sperm revealed an identical stain morphology in a variant of the present assay. Samples of human sperm were provided from a healthy donor. An expert in sperm quality assessment examined a sample by light microscopy and determined that it was typical in morphology and motility. Next, an assay was performed on aliquots of neat semen, which were evaluated by bright field and fluorescence microscopy. To prepare sample, 100 ul of neat semen and 400 ul of phosphate buffered saline pH 7.0 were mixed and centrifuged for 2 minutes at 3,000 rpm in an Eppendorf 5415C minifuge with fixed angle rotor. Supernatant was aspirated and one additional wash of 400 ul Phosphate Buffered Saline (PBS) was performed. The cells were resuspended in 300 ul PBS. 100 ul of washed cells were transferred to a clean tube to which was added 150 ul PBS, 6 ul of 1 mg/ml murine anti-human calponin monoclonal antibody (gift from Dr. E. Mabuchi, Boston Biomedical Research Institute) and 12 ul goat anti-mouse IgM-AlexaFluor 488 (Invitrogen Corporation, Cat. no. A21042, 2 ug/ml). The tube was incubated at room temperature for 30 minutes.

Then 1 ml PBS was added and the tube was centrifuges in the minifuge.

Supernatant was aspirated, 250 ul PBS was added and aliquots were examined by bright field and fluorescence microscopy. A punctate pattern of labeling over the acrosomal region was noted, with some post-acrosomal labeling at the midpiece. In some cases, a small amount of very bright punctate labeling with weak midpiece labeling was noted.

This pattern is similar to that noted with bull sperm in the present assay, with the exception that in the present assay labeling is brighter and is confined to the acrosomal region.

Other Markers of Cell Surface Changes

Sperm cell surface changes that have been reported and can be monitored according to the present assay including, but preferably not limited to increases in net negative surface charge (Bedford (1963) *Nature* 200: 1178-1180; Yanagimachi et al. (1972) *Am J Ant.* 135:497-520; Lopez et al. (1989) Gamete Res. 18:319-332), changes in glycoprotein amount or localization (Baker et al. (2004) *J Andrology* 25:744-751), changes in cholesterol and lipid distribution (Wolfe et al (1998) *Biol Reprod* 59:1506-1514; Flesch et al (2001) *J Cell Sci* 114:3543-3555) and phosphatidylserine location (Pena (2007) *Asian J Androl* 9:731-737). For example, since sperm develop a net negative surface charge over time, positively charged proteins can be conjugated to an appropriate fluorophore for evaluation. Suitable proteins have a pI greater than or equal to 8.5 so that they will be positively charged at the pH of the binding assay and include histidine-rich proteins such as the late embryogenesis abundant (LEA) proteins (Moons et al. (1995) *Plant Physiol* 107:177-186). Similarly, lectins conjugated to a fluorophore can be used such as *Pisum sativum* lectin (PSA), tomato lectin (LEA), peanut lectin (PNA), *Aleuria aurantia* agglutinin lectin (AAA), *Ulex europaeus* agglutinin lectin (UEA-1), wheat germ lectin (WGA), *Solanum tuberosum* (STA) and *Tetragonobolus lectin* (TPA). Mono- or oligosaccharides suitable for conjugation to a fluorophore include those terminating at the non-reducing end in fucose, galactose, or mannose, or being polymers of lactose-aminoglycans.

Other Markers

Alternatively, the metabolic status of semen is assayed by markers assessing sperm quality. One marker of sperm quality is measured on the basis of sperm motility grade and percent. Another marker of sperm quality is measured on the basis of the number of intact acrosomes.

Incubation Conditions

The methods of monitoring the metabolic status and/or desired traits of the semen sample involve are performed as the semen sample is incubating. Typically, the semen sample is incubated in a suitable collection container which has an overall and uniform temperature equivalent to the ambient temperature or falling within some range with a low temperature not lower than 0° C. and a high temperature not higher than the body temperature of the pertinent species or the ambient temperature. In one embodiment the semen sample is cooled from a collection temperature of approximately 35° C. to 12° C., where the incubation is then maintained at a constant temperature of 12° C. +/−0.1° C. In other embodiments the sample may be cooled from a collection temperature of approximately 35° C. to any of the following temperatures (+/−0.1° C.) at which the incubation is maintained at a constant temperature until the semen sample is collected for use, e.g., packaging into straws: (34° C., 33° C., 32° C., 31° C., 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., 0° C., and any temperature point in between. In alternate embodiments, the variation of the constant incubation temperature includes, but preferably is not limited to, +/−0.1° C., +/−0.2° C., +/− 0.3° C., +/−0.4° C., +/−0.5° C., and +/−1.0° C. The devices disclosed in application PCT/US09/38134 or in US 2006/0147894 A 1 are examples of suitable collection containers, as is the device disclosed in U.S. Pat. No. 5,895,749. Application PCT US09/38134 is hereby incorporated by reference in its entirety. In one embodiment, the incubation temperature is not held constant, but varies according to a defined pattern or cycle of temperature intervals, the incubation at each interval being maintained at a specified temperature for a specified duration.

In one embodiment, the methods described herein provide a means for determining when to process semen samples, for example, by extending and aliquoting the semen sample into straws, for freezing or immediate use, e.g., in artificial insemination. Various reagents and physical conditions to which sperm may be exposed during processing, can affect sperm metabolism. The present assay also provides a means of evaluating treatments most beneficial to sperm and enabling users to improve sperm quality and properties in commercial operations by use of an optional treatment. The treatment minimizes variability in the sperm microenvironment within the semen ejaculate. For example, variability can result from the fact that, in some species, different pulses of ejaculate have very different biological compositions and, consequently, there is a gradation within the chemical microenvironment. In other cases the variability is a result of temperature or chemical differences within the semen sample. Therefore, the treatment that homogenizes the semen collection can comprise contact with chemical agents such as, for example, glycosidases (e.g. sialidase, galactosidase, glucosidase, and/or mannosidase), perioxidase, and/or horseradish peroxidase), proteases (e.g. chymortipsin, trypsin, and/or elastase), lipases (e.g. phospholipase C and/or phospholipase A) and kinases (e.g. diglyceride kinase, glycogen synthase kinase and/or inositiol kinase), to name but a few, and/or mono- or oligosaccharides, etc., or incubation at particular temperatures. Suitable temperatures can be any temperature between 0° C. and the ambient and/or the body temperature, or for example, between 0° C.-40° C., 15° C.-40° C., 18° C.-25° C., 25° C.-30° C. 4° C.-40° C., 15° C.-40° C., 18° C.-25° C., or 25° C.-30° C., to name but a few. However, preferably, incubation is maintained at a preselected temperature ±1° C., or ±2° C. Treatment can also comprise gentle mechanical mixing such as slow rocking of the tube, use of a rotary shaker, or tube inversion Combinations of any of the above treatments that homogenize the semen environment are also envisioned.

Mono- or oligosaccharides can be added to the semen collection sample after having been equilibrated to the same temperature as the collection sample. Ideally, this is done at the time of collection, but can be done at any time during the incubation step. Suitable mono- or oligosaccharides are carbohydrates that resemble those present in the isthmus. It is known that the isthmus of the oviduct can serve as a site of sperm binding to create a reservoir of sperm, which are presumed to be in a stabilized state. The mono- or oligosaccharides are chosen to effect membrane stabilization, which stabilize sperm against the manipulations they must undergo. Suitable monosaccharides include sialic acid, mannose, fucose or galactose, while appropriate oligosaccharide polymers are linear or branched chains of any compatible sugar or glycoproteins carrying carbohydrate chains that terminate at their non-reducing end in fucose, galactose, sialic acid or a combination of these sugars. Additional suitable treatments include commercial semen diluents and extenders, TALP, glycerol, egg yolk, bicarbonate ions and calcium ions or calcium chelators. Combinations of the above can also be used.

Additional treatments include the addition of a sugar polymer, a lipid, an enzyme or combinations thereof is added. Another treatment changes the temperature of the semen sample. Yet another treatment is mechanical agitation of the semen sample. In some embodiments multiple treatments of the same or different types are performed at the same time or are preformed sequentially.

With respect to the treatment, one embodiment envisions a treatment where a sugar polymer, a lipid, an enzyme or combinations thereof is added. Another embodiment uses a treatment that changes the temperature of the semen collection. In yet another embodiment the treatment is mechanical agitation. In some embodiments multiple treatments of the same or different types are performed at the same time or are preformed sequentially.

Processing

Once the results of the assessment of fertility and/or the generation of a sex bias are obtained, the semen is washed and diluted (extended) using commercially available products such as Bioxcell® (IMV, L'Aigle, France), or egg yolk based extenders, or the extenders Triladyl® and Andromed® (Minitube, Tiefenbach, Germany) before packaging into straws.

Kit

One embodiment comprises a kit for carrying out the disclosed assay. The kit contains at least a first binding protein and a description of the method. In some embodiments the kit further comprises for example, a dye, or at least a first binding protein and optionally a second binding protein, and a sampling container and/or incubator. Further, the kit contains instructions for observing morphological changes that reflect the metabolic changes used to predict field traits, for instance by brightfield microscopy.

Summary

The methods described herein are designed for smooth integration into current methods of semen processing (see FIG. 1) and, when properly implemented as described herein, create an increase in fertility and/or a sex bias in a time-based method. Preferably, this occurs under conditions that maintain fertility in standard on-site techniques of artificial insemination. The method preferably preserves the number of cells processed, because methods that cause a reduction in cell yield are unsuitable in terms of economic and fertility losses. All methods requiring a physical separation of sperm reduce cell yield.

The present methods preferably achieve increased fertility and/or creation of a gender bias by enabling detection of sperm metabolic changes that indicate when collected semen should be processed. As shown in FIG. 13, assay results enable users to process semen at a time that can increase fertility and/or cause sex bias, and/or have another desirable trait upon artificial insemination (AI).

WORKING EXAMPLES

Example 1

Annexin Treatment

The sperm from a 10 µl sample of ejaculate is washed twice with PBS buffer (8 g NaCl; 0.2 g KCl; 1.44 g $Na_2HPO_4 \cdot 7H2O$; 0.24 g $KH_2PO_4$; $H_2O$ to 1 liter. pH 7.2) and the cells resuspended at a concentration of ~$1 \times 10^6$ cells/ml in 1× Binding Buffer (10× Buffer is 0.1 M HEPES, pH 7.4; 1.4 M NaCl; 25 mM $CaCl_2$).

100 µl of the solution (~$1 \times 10^5$ cells) is transferred to a 5 ml culture tube and 2 µl of Annexin V stock solution (Annexin V-PE; BD Biosciences cat. no. 556422, 556421) added. The cells are gently mixed and incubated for 5 min. at room temperature in the dark. 400 µl of 1× Binding Buffer is added and the cells analyzed immediately by fluorescence microscopy to determine the number of cells positive for apoptosis (i.e. Annexin V positive).

Controls are (1) unstained cells, (2) experimental cells stained with Annexin V-FITC for 5 min. and (3) blocked cells stained with 5 mg of unlabeled Annexin V and then Annexin V-FITC. Annexin A5 is used as a probe to detect cells that have expressed phosphatidylserine on the cell surface, a feature found in apoptosis as well as other forms of cell death Blocked Cell Control This control includes preincubation of cell samples with recombinant unconjugated Annexin V, which is included as part of the BD Annexin V-FITC Apoptosis Detection Kit II (Cat. No 556570). This serves to block Annexin V-FITC binding sites and thus demonstrates the specificity of Annexin V-FITC staining.

The protocol is essentially as described above, but 5-15 µg of purified recombinant Annexin V is added instead of Annexin V-PE. The amount of purified recombinant Annexin V required to saturate binding sites may vary according to cell type, and stage of apoptosis. In some cases the cell number is reduced to $0.5 \times 10^5/100$ µl, still adding 5-15 µg of recombinant Annexin V, to obtain optimal results. In addition, the resulting Annexin V mixture is incubated at room temperature for 15 minutes before adding 5 µl of Annexin V-FITC, mixing and incubating again at room temperature for 15 minutes in the dark. 400 µl of 1× Binding Buffer is added and the cells analyzed immediately by fluorescence microscopy.

Increased sex bias is produced, in the case of annexin V, using a jump point when 20-40% of sperm show annexin V positivity.

Example 2

Semen Preparation and Processing

A device according to PCT/US09/38134 was incubated at 32° C. for 60 minutes or more to ensure uniform heating of the device. Just prior to use, the device was removed and within 2 minutes of collection, the sperm was placed in the collection container, inverted once, then immediately placed at 12° C. for at least 15 minutes before sampling is begun. During the sampling time the collection of sperm is maintained at 12° C.

5 µl of undiluted semen is mixed in a 1.5 ml microfuge tube with 100 µl antibody diluent with Bovine Serum Albumin (Invitrogen SKU #00-3118). Twenty (20) µl of primary antibody (rabbit anti-*Salmonella* spp; *Salmonella* H antiserum A-Z product number 224061; Difco, Detroit, Mich.; reconstituted according to the manufacturer's instructions) is added, followed by 5 µl of secondary antibody conjugated to Alexa Fluor® 488 (goat anti-rabbit IgG (H+L); Invitrogen, Carlsbad, Calif., catalogue no. A11008) (2 mg/l) and mixed. The solution is then incubated in the dark for 20-30 minutes at ambient temperature. In general, the ambient temperature ranged from 7° C.-27° C.

After incubation, 1 ml of PBS buffer (8 g NaCl; 0.2 g KCl; 1.44 g $Na_2HPO_4 \cdot 7H2O$; 0.24 g $KH_2PO_4$; $H_2O$ to 1 liter. pH 7.2) is added and the solution microfuged for 20 seconds before removing the supernatant. The cell pellet is gently resuspended in 100 µl of PBS buffer and approximately 5 µl transferred to a microscope slide. The number of sperm exhibiting green fluorescence on the head (deemed "positive") is counted as well as the total number of cells. A minimum of 100 cells are counted and the "percent positive" (% positive) is determined by dividing the number of positive cells by the total number of cells and multiplying by 100.

In this case, the processing time is determined based on the % positive. If there are less than 25% positive, incubation is continued for approximately 1 hour before repeating the assay. If more than 25% positive, the assay is repeated at a shorter time interval such as 5, 10 or 15 minutes. Values of the % positive reach a peak and then begin to decline. Two hours after the peak, Bioxcell® extender or egg yolk-based phosphate buffer extender equilibrated to 12° C. is added to the semen, semen is cooled to 4° C.-10° C. and semen is processed into straws or used immediately. Any method can be used for processing into straws, including methods described in by P. Bermejo-Alaverez et al. (2008) *Biol of Reproduction* 79:594-597).

Example 3

Variability of Sperm Biology

Figure 5:
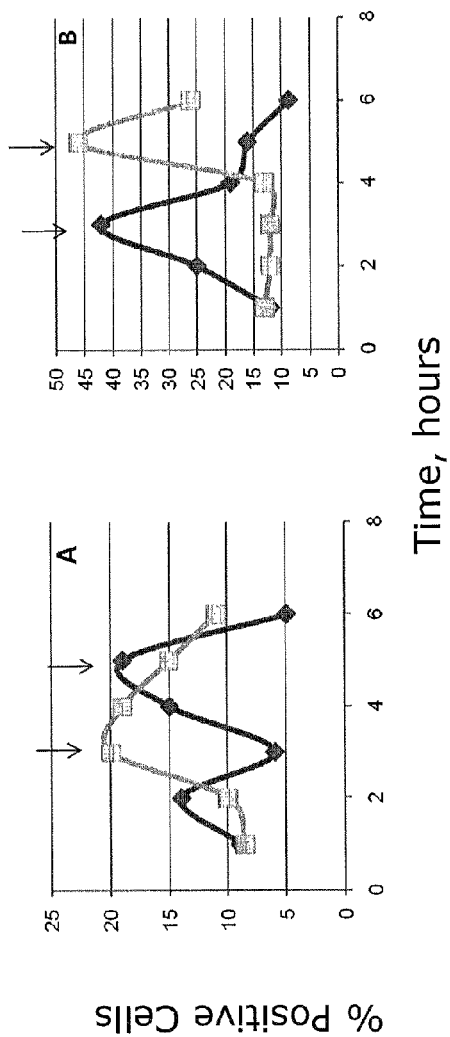
FIG. 5. Process Control Assays Sperm Cell Assays Reveal High Variability. (A) assay of collections on two different days from a Canadian Holstein bull. (B) assay of collections on two different days from a Friesian bull. X axes are percentage of cells which are positive for the marker. Y axes are time of neat semen incubation.

Semen was collected from dairy bulls (time=0) and incubated. At intervals, samples were taken and assayed according to Example 2. (A) assay of collections on two different days from a Canadian Holstein bull named Bacardi. (B) assay of collections on two different days from an Irish Friesian bull named RDU. Results are presented in FIG. 5.

Variability of sperm cell biology between bulls and between collections is revealed by the large differences in assay curve shape and in the time required for attainment of the assay peak point.

Example 4

Figure 10:
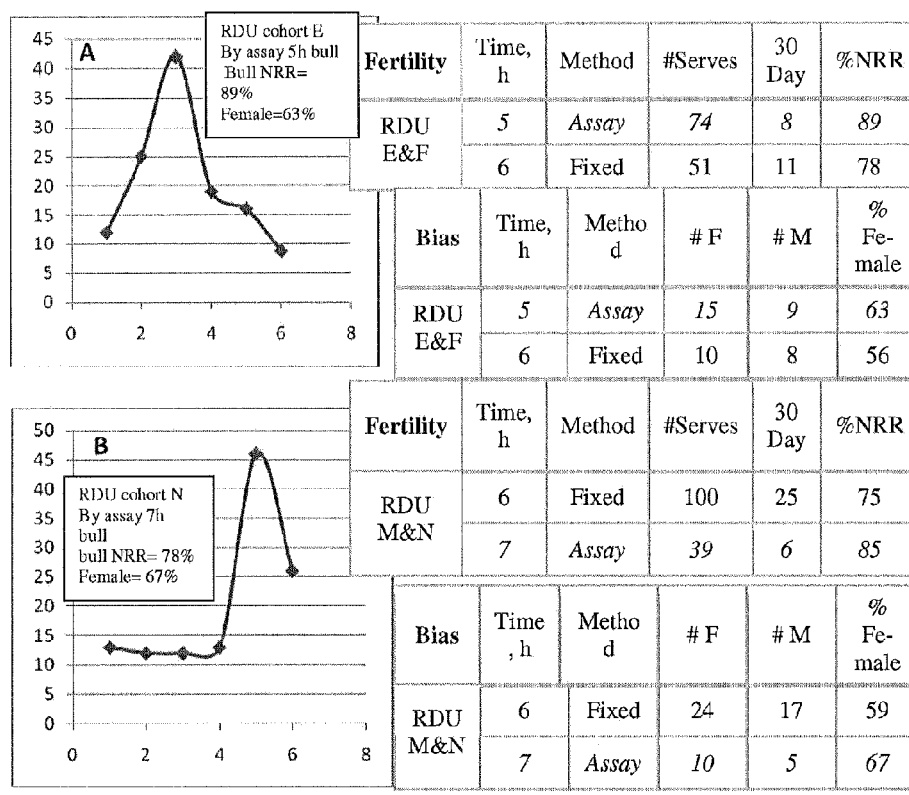

Fertility and Gender Bias Increases in Working Dairy Herds Correlates with Assay Peak Point The first ejaculate of Freisian bull RDU was collected on two different days as shown in FIG. 10 (A) and (B). On each day, half of the ejaculate was processed at 6 h. The other half of the ejaculate was processed according to Example 2. In FIG. 10 (A) bull RDU collection was processed into cohorts RDU-E (assay-based, 5 hour incubation) and RDU-F (fixed time, 6 hours). In FIG. 10B, bull RDU collection was processed into cohorts RDU-M (fixed time, 6 hours) and RDU-N (assay-based, 7 hours incubation). A fertility difference of about 10% was observed between the two processing methods, independent of whether the assay indicated processing time should occur before or after the fixed 6 h time point. Results for gender bias and fertility appear in Examples 5-7 below.

Example 5

Fertility Increase in Working Dairy Herd

The first ejaculate of elite dairy bulls was collected and sperm cells assayed according to a "fixed time" incubation process or according to Example 2. For fixed time incubation, 12° C. extender was added to the 12° C. incubated semen and processed into frozen straws 6 hours post-collection. For semen assayed according to Example 2, the incubated semen was extended and processed into straws 2 hours after the assay revealed a peak in the percentage of assay-positive sperm (% positive). The time at which this peak was obtained varied between collections.

Two bulls were collected on different days to obtain semen treated by incubation. The control treatment involved the same two bulls with the collections of semen being processed into frozen straws according to standard methods. Success was measured by the non-return rate (NRR) of cows and heifers. NRR is a measure of fertility and is the percentage of animals in the dairy herd that do not return for repeat insemination due to pregnancy or death. A high NRR correlates with high herd fertility and is desirable.

Table 1 presents the results obtained and reports the number of animals serviced through AI, the number of animals returned after 30 days due to failure to become pregnant and the percent of non-return rate (% NRR). The normal heat cycle of a cow is 21 days.

TABLE 1

Increased Fertility in Working Dairy Herd

| Treatment | Incubation method | #Serves | 30 Day | % NRR |
|---|---|---|---|---|
| Control | n/a | 1010 | 158 | 84.36 |
| Incubation | Fixed time | 164 | 38 | 76.83 |
|  | Assay-based | 139 | 18 | 87.05 |

From the results presented it is clear that sperm obtained from the assay and used for insemination produced a greater number of pregnancies; that is, as a population had increased fertility. For example, in the fixed time group, 164 animals were serviced by artificial insemination. By 30 days after initial service, 38 of these were returned for repeat insemination, as they were not pregnant. About 77% of the animals were therefore NOT returned for repeat insemination, giving a 76.8% non-return rate. In contrast, for the assay group, 139 animals were inseminated and only 18 were returned for repeat insemination by day 30, meaning 87% of the animals were not returned for repeat insemination.

In the control group, the non-return rate was 84.36% while in the assay group the NRR was 87.05, which indicates a fertility improvement of 2.69%. The fixed time group showed damage to fertility. Using logistic regression with pregnancy as the outcome, the improvement obtained by the assay method is statistically significantly more likely to increase fertility than the fixed time method (log odds ratio=0.71, p=0.047; a log odds ratio of 0 implies no association).

Example 6

Fertility Increase Requires Incubation Time Variability

In order to determine the effect of incubation on fertility, the first ejaculate of two elite dairy bulls, RDU and QUR was collected. Each semen collection from each bull was divided in half. One half of the collection was processed according to a "fixed time" incubation process and one half according to Example 2. For the fixed time incubation, 12° C. extender was added to the 12° C. incubated semen and processed into frozen straws 6 hours post-collection. For semen assayed according to Example 2, the incubated semen was extended and processed into straws 2 hours after the assay revealed a peak in the percentage of assay-positive sperm (% positive).

Table 2 presents the data obtained and reports the number of animals serviced through AI, the number of animals returned after 30 days due to failure to become pregnant (NNR) and the percent of non-return rate (% NRR). The normal heat cycle of a cow is 21 days.

TABLE 2

Fertility Increase Is Correlated With Assay

| Collection Pair and Bull | Time, h | Method | #Serves | 30 Day | % NRR |
|---|---|---|---|---|---|
| RDU | 6 | Fixed | 51 | 11 | 78 |
| E&F | 5 | Assay | 74 | 8 | 89 |
| QUR | 6 | Fixed | 8 | 2 | 75 |
| I&J | 7 | Assay | 20 | 3 | 85 |
| RDU | 6 | Fixed | 100 | 25 | 75 |
| M&N | 7 | Assay | 39 | 6 | 85 |

The data in Table 2 indicates that the quality of the sperm obtained from the assay method results in more pregnancies and a lower % NRR.

Example 7

Gender Bias in Working Dairy Herd

In order to determine the effect of incubation on gender bias, the first ejaculate of elite dairy bull RDU was collected as described in Example 3. Each semen collection was divided in half. One half of the collection was processed according to a "fixed time" incubation process and one half according to Example 2. For the fixed time incubation, 12° C. extender was added to the 12° C. incubated semen and processed into frozen straws 6 hours post-collection. For semen assayed according to Example 2, the incubated semen was extended and processed into straws at the time shown in Table 3 (e.g. 2 hours after the assay revealed a peak in the percentage of assay-positive sperm (% positive).

Table 3 presents the data obtained and reports the numbers of each gender produced as determined by fetal scanning.

TABLE 3

Gender bias according to fetal scanning

| Collection Cohorts and Bull | Time, h | Method | # Females | # Males | % Female |
|---|---|---|---|---|---|
| RDU- E&F | 5 | Assay-based | 15 | 9 | 63 |
| | 6 | Fixed | 10 | 8 | 56 |
| RDU- M&N | 6 | Fixed | 24 | 17 | 59 |
| | 7 | Assay-based | 10 | 5 | 67 |

As can be seen from the results, the assay-based treated semen in accord with the present invention produced more females, as desired, than the fixed time treatment.

Table 4 summarizes the results obtained when the data from Table 3 is grouped according to fixed-time or assay-based treatment.

TABLE 4

Summary of gender bias based on semen treatment

| Treatment | Incubation method | # Females | # Males | % Female* |
|---|---|---|---|---|
| Control | n/a | n/a | n/a | 50 |
| Incubation | Fixed time | 34 | 25 | 58 |
| | Assay-based | 25 | 14 | 64 |

*for control, historical percentage of females is reported

Example 8

Semen Preparation and Processing—Enzymatic

A device according to PCT/US09/38134 is incubated at 32° C. for 60 minutes or more to ensure uniform heating of the device. Just prior to use, the device is removed and within 2 minutes of collection, the sperm is placed in the collection container, inverted once, then immediately placed at 12° C. for at least 15 minutes before sampling is begun. During the sampling time the collection of sperm is maintained at 12° C.

20 µl of undiluted semen is mixed in a 1.5 ml microfuge tube with 1000 µl antibody diluent with Bovine Serum Albumin (Invitrogen SKU #00-3118). Five (5) µl of primary antibody (e.g. rabbit anti-*Salmonella* spp; *Salmonella* H antiserum A-Z product number 224061; Difco, Detroit, Mich.; reconstituted according to the manufacturer's instructions) is added, mixed and incubated in the dark for 15 minutes at ambient temperature. 10 µl as supplied by the manufacturer of a peroxidase-conjugated goat anti-rabbit IgG (H+L) (catalogue no. Invitrogen SKU # G-21234) secondary antibody is added.

After incubation, 1 ml of PBS buffer (8 g NaCl; 0.2 g KCl; 1.44 g $Na_2HPO_4 \cdot 7H_2O$; 0.24 g $KH_2PO_4$; $H_2O$ to 1 liter. pH 7.2) is added, the resulting solution mixed gently and centrifuged. The supernatant decanted. This wash step is repeated five times.

To produce signal, 1 ml of peroxidase soluble substrate (TMB/E Ultra Sensitive, Blue, Horseradish Peroxidase Substrate (soluble); Millipore) is added, mixed gently and incubated at ambient temperature for 10 minutes.

The tube is placed in a calibrated colorimeter and the absorbance reading taken.

Proportionally smaller volumes can be used to accommodate performing the assay in a 96 well format or other configurations.

The processing time is determined based on the optical density (OD) reading. Incubation is continued for approximately 1 hour before repeating the assay. Once the OD reading has increased by about 20% above background, the assay may be repeated at a shorter time interval such as 5, 10 or 15 minutes. With time, the OD reading will again decline. Two hours after the peak OD reading, Bioxcell® extender or egg yolk-based phosphate buffer extender equilibrated to 12° C. is added to the semen, semen is cooled to 4° C.-10° C. and semen is processed into straws or used immediately.

Example 9

Gender Bias from In Vitro Fertilization Studies

Semen was collected from an elite diary bull, KSY, and was either placed into a jacketed collection tube pre-warmed to 32° C., which was then placed and held at 12° C. (i.e. control), or processed as described in Example 2.

In vivo analysis of fixed time and assay-based artificial insemination of working herds was conducted. Based on fetal screening, the assay-based method gave higher gender bias than the fixed-time method. In contrast, during in vitro analysis of single fixed time and assay-based incubations, the fixed incubations gave higher gender bias than assay-based. In both cases, however, the percent female embryos is elevated above baseline by in vitro analysis. Table 5 presents the results of in vitro analysis.

TABLE 5

Gender bias detected by in vitro fertilization of bovine eggs, followed by PCR-based gender analysis.

| Treatment | Male n (%) | Female n (%) | Not sexed n (%) |
|---|---|---|---|
| Control | 77 (59.2) | 53 (40.8) | 1 (0.7) |
| Assay-based | 77 (57.9) | 56 (42.1) | 1 (0.7) |
| Fixed time | 60 (51.3) | 57 (48.7) | 2 (1.7) |
| Total | 214 (56.3) | 166 (43.7) | 4 (1) |

Example 10

Gender Bias Produced in Field Trials

Nine ejaculates from 5 bulls were processed by two variants of the method in accordance with the present invention. Cows and heifers were serviced by standard Art Insemination. Fetal Scanning was performed to evaluate calf gender. National Irish Cattle Breeding Federation (ICBF) records were used for controls.

The Field Trial results are shown below.

TABLE 6

Gender Bias is Produced and is Statistically Significant

| Treatment | Total Births | # Female Births | # Male Births | Percentage Female |
|---|---|---|---|---|
| Control | 36,674 | 18,443 | 18,231 | 50% |
| Methods Described herein | 498 | 285 | 213 | 57% P = 0.001 |

A statistical analysis of these results indicates that the null hypothesis that the gender bias in the experimental group is equivalent to the gender bias in the control group can be rejected with a two-sided P-value of 0.001 from a chi-square test of equality of proportions. The confidence interval means that, with probability of 95%, the true gender bias is between 53% and 62%.

Example 10

Fertility is Maintained in the Present Methods Producing Gender Bias Produced in Field Trials Ten collections of semen were obtained from 5 bulls and processed by either control or a method of the present invention. (One bull—one collection—was later eliminated due to excessive broken heads, and one for abnormal assay curve). Cows and heifers were serviced by standard Artificial Insemination. National Irish Cattle Breeding Federation (ICBF) records were used for NRR.

TABLE 7

Control Fertility and Fertility Generated by the methods described herein are Statistically Indistinguishable

| Treatment | Total Births | 60 Day NRR | 60 Day % |
|---|---|---|---|
| Control Methods | 1,469 | 335 | 0.7583 |
| Methods described herein | 1,469 | 388 | 0.7359 |

Statistical analysis of the field trial results above indicates that using a two-sided, 0.05 level Fisher's exact test, the control and experimental cohorts are not significantly different (p=0.174).

All patents, patent applications, and published references cited herein are hereby incorporated by reference in their entirety. The disclosure set forth herein has been particularly shown and described with references to preferred embodiments thereof, it will be understood by those skilled in the art that various changes in form and details may be made therein without departing from the scope encompassed by the appended claims.

The invention claimed is:

1. A method of processing semen for administration to an egg or a female mammal or combination thereof, wherein the processed semen has an increased percentage of sperm having a desired trait, the method comprising:
    a) collecting an ejaculate of semen;
    b) monitoring in real-time the metabolic status of sperm in the ejaculate during incubation under controlled conditions prior to processing for artificial insemination or in vitro fertilization by measuring at a plurality of time points the expression of a biomarker that is indicative of the metabolic status of the semen, wherein the controlled conditions includes cooling the collected ejaculate of semen from a temperature ranging from the body temperature of the particular species from which it was collected to a temperature not less than about 0° C.;
    c) determining a jump point based on the expression level of the biomarker for the sperm in the ejaculate; and
    d) applying a time shift from the jump point identified by the real-time monitoring of biomarker expression;
    wherein the method for determining the time shift for processing the ejaculate for artificial insemination or in vitro fertilization comprises the steps of:
        i) selecting a biological marker that is indicative of a metabolic status of sperm having said desired trait, wherein expression of the biological marker changes during said incubation,
        ii) determining the level of expression of the biomarker by sperm of a prior ejaculate during a prior incubation under the same controlled conditions at a plurality of time points during prior incubation, wherein an aliquot of said prior ejaculate is assayed at each time point,
        iii) determining a maximum time point when the sperm in the prior ejaculate display a maximum level of expression of said biomarker,
        iv) selecting a prior time point (jump point) which occurs before the sperm in the prior ejaculate display the maximum level of the desired trait,
        v) determining the level of expression of the biomarker by sperm in the prior ejaculate at the selected prior time point (jump point);
        vi) determining the elapsed time between the jump point and the maximum level of the desired trait of step (iv), thereby providing a value for a time shift for a change in the metabolic status between the jump point and the maximum level of the display of the desired trait,
    e) processing said semen ejaculate at a later time, wherein said later time is determined by adding the time shift to the jump point time determined in previous step (iv), wherein said processing for in vitro fertilization or artificial insemination does not comprise physically separating the cells based on said desired trait, thereby obtaining semen with an increased percent of sperm with the desired trait, and
    f) administering the semen with the increased percent of sperm with the desired trait to an egg, a female mammal or combination of thereof by an in vitro fertilization or artificial insemination method.

2. The method of claim 1, wherein said desired trait is selected from the group consisting of female gender bias in said sperm, male gender bias, fertility, and a combination thereof.

3. The method of claim 1, wherein said sample is assayed for said marker at intervals ranging from 5 minutes up to and including 8 hours.

4. The method of the claim 1, wherein said marker is selected from the group consisting of a cell surface ligand, an enzyme and a receptor.

5. The method of claim 1, wherein said marker is a cell surface marker, and wherein said jump point occurs when expression of said marker in said sample is less than its maximal expression by a percentage ranging from 95% to 25% as determined by the assay of step ii).

6. The method claim 1, wherein determining the level of expression of said marker by sperm of said prior ejaculate comprises determining the percentage of sperm expressing said marker detected in sperm of said prior ejaculate, said determining comprising:
   a) removing an aliquot from the prior ejaculate;
   b) contacting the aliquot with a first ligand to said marker;
   c) detecting binding of said ligand by said sperm; and
   d) determining the amount of marker expressed by sperm in said aliquot by quantitating the binding of the marker by the ligand;
   thereby determining the percentage of sperm expressing said marker detected in sperm of said semen sample.

7. The method of claim 6, wherein said ligand is labeled.

8. The method of claim 7, wherein detecting the binding of said first ligand by said sperm in step c) of claim 6 comprises detecting said label.

9. The method of claim 6, wherein detecting the binding of said first ligand by said sperm in step c) of claim 6 comprises contacting said sperm in said aliquot with a second ligand which binds to said first ligand.

10. The method of claim 6, wherein the binding of said first ligand evokes the appearance of a secondary marker, further comprising contacting said secondary marker with a supplemental ligand.

11. The method of claim 10, wherein said first ligand and/or said second ligand and/or said supplemental ligand is an antibody.

12. The method of claim 11, wherein said antibody is a polyclonal antibody.

13. The method of claim 11, wherein said antibody is a monoclonal antibody.

14. The method of claim 11, wherein said antibody comprises a detectable label.

15. The method of claim 14, wherein said label is a fluorophore.

16. The method of claim 15, wherein the fluorophore is selected from the group consisting of carboxyfluorescein acetate, phycoerythrin, calcein acetate, YO-PRO-1, SNARF-1, AlexaFluor-488, FITC and combinations thereof.

17. The method of claim 11, wherein said first ligand is an anti-salmonella polyclonal antibody and the second ligand is selected from the group consisting of an antibody that recognizes IgG and an antibody that recognizes IgM.

18. The method of claim 6, wherein said marker is a phospholipid and said ligand is Annexin V.

19. The method of claim 18, wherein said Annexin V is labeled.

20. The method of claim 1, wherein said monitoring is on-site.

21. The method of claim 1, wherein said processing consists of diluting and aliquoting said semen sample for storage or immediate use.

22. The method of claim 1, wherein the controlled conditions includes cooling the collected ejaculate of semen stepwise from a temperature ranging from the body temperature of the particular species from which the semen was collected to a temperature not less than about 0° C.

23. The method of claim 1, wherein the controlled conditions includes cooling the collected ejaculate of semen stepwise from a temperature ranging from the body temperature of the particular species from which the semen was collected, to ambient temperature, to a temperature not less than about 0° C.

24. A method of processing semen for administration to an egg or a female mammal or combinations thereof, wherein the processed semen has an increased percentage of sperm having a desired trait without physically separating the sperm having the desired trait from the remaining semen, the method comprising:
   a) collecting an ejaculate of semen;
   b) monitoring in real-time the metabolic status of sperm in undiluted ejaculate during incubation under controlled conditions prior to processing for in vitro fertilization or artificial insemination by measuring at a plurality of time points the expression of a biomarker that is indicative of the metabolic status of the semen wherein the controlled conditions includes stepwise cooling the collected ejaculate of semen from a temperature ranging from the body temperature of the particular species from which it was collected to a temperature not less than about 0° C.;
   c) determining a jump point based on the expression level of the biomarker for the sperm in the ejaculate;
   d) applying a time shift from the jump point identified by the real time monitoring of biomarker expression;
   e) processing said semen ejaculate after the time shift point wherein said time shift point is determined by adding the time shift to the jump point time; and
   f) administering the semen with the increased percent of sperm with the desired trait to an egg, a female mammal or combination thereof by in vitro fertilization or artificial insemination method.

* * * * *